United States Patent [19]
Stierle et al.

[11] Patent Number: 5,908,759
[45] Date of Patent: *Jun. 1, 1999

[54] TAXOL PRODUCTION BY A MICROBE

[75] Inventors: Andrea Stierle; Donald Stierle, both of Butte; Gary Strobel, Bozeman, all of Mont.

[73] Assignee: The Research and Development Institute at Montana State University, Bozeman, Mont.

[ * ] Notice: This patent is subject to a terminal disclaimer.

[21] Appl. No.: 08/979,476

[22] Filed: Nov. 26, 1997

Related U.S. Application Data

[60] Division of application No. 08/258,105, Jun. 10, 1994, Pat. No. 5,861,302, which is a continuation-in-part of application No. 07/971,508, Nov. 4, 1992, Pat. No. 5,322,779, which is a continuation-in-part of application No. 07/869,726, Apr. 16, 1992, abandoned.

[51] Int. Cl.$^6$ .............................. C12P 17/02; C12N 1/14

[52] U.S. Cl. .............................. 435/34; 435/117; 435/123; 435/132; 435/147; 435/155; 435/171; 435/254.1; 549/510; 549/511

[58] Field of Search .............................. 435/34, 123, 117, 435/132, 171, 254.1, 147, 155; 549/510, 511

[56] References Cited

U.S. PATENT DOCUMENTS

| | | |
|---|---|---|
| 4,206,221 | 6/1980 | Miller et al. . |
| 4,468,458 | 8/1984 | Sato et al. . |
| 5,019,504 | 5/1991 | Christen et al. . |
| 5,322,779 | 6/1994 | Strobel et al. .......................... 435/123 |

*Primary Examiner*—Leon B. Lankford, Jr.
*Attorney, Agent, or Firm*—McDermott, Will & Emery

[57] ABSTRACT

Taxol is produced from taxol-producing microorganisms. Methods of obtaining the taxol-producing microorganisms are described. Radioactive labelled taxol products and methods for use of the radioactive labelled taxol and for the treatment of leukemia and cancer cells are described.

6 Claims, 19 Drawing Sheets

1ND 1000x

H10BA2 1000x

WIC65NC 1000x

CC45BD 1000x

CC50NA1 1000x

CC54BE 1000x

CC64BB 1000x

CC54BA 1000x

CC53NA2-1 1000x

CC52NC 1000x

TAXOL PRODUCTION BY A MICROBE

This application is a division of application Ser. No. 08/258,105, filed Jun. 10, 1994, now U.S. Pat. No. 5,861,302 which is a continuation in part application of Ser. No. 07/971,508 filed Nov. 4, 1992, now U.S. Pat. No. 5,322,779, issued Jun. 21, 1994, which is a continuation in part of application Ser. No. 07/869,726, filed Apr. 16, 1992, now abandoned.

This invention was made with support under Grant No. DHE-9206803 (NSF) awarded by the National Science Foundation.

TECHNICAL FIELD

The present invention relates to the use of one or more microorganisms to produce taxol (and related taxanes). The invention discloses the method of the discovery of said microorganisms, their isolation, screening for taxol production, growth requirements for taxol production, and chemical evidence for taxol (taxane) production.

BACKGROUND OF THE INVENTION

Taxol, which is of the chemical structural formula:

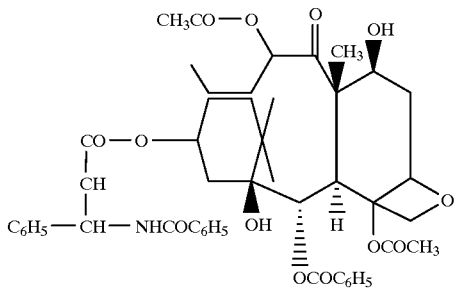

shows significant properties of promoting the polymerization of tubulin and inhibiting the depolymerization of microtubules. For these reasons, taxol is a valuable antileukemic and antitumor agent and is the subject of increasing research.

Taxol is known to be extracted from the trunk bark of different species of the Taxus, or Yew tree. Yields are generally low, usually on the order of no more than about 100 milligrams per kilogram in the extraction process. Various procedures for the production of taxol are known for example, from U.S. Pat. Nos. 4,814,470 and 4,857,653. A chemical process for the preparation of taxol is disclosed in U.S. Pat. No. 4,924,011.

Wani et al, "Journal of the American Chemical Society", Vol. 93, May 1971, No. 9, pages 2325–2327, reports on the structure of taxol and its potential use as an antileukemic and tumor inhibitory compound. This publication further discusses an alcohol extraction procedure for obtaining taxol from the stem bark of the western Yew tree (*Taxus brevifolia*).

The Pacific yew, *Taxus brevifolia*, is one of only ten Taxus species known worldwide. It is not confined to the Pacific coast of North America as its name might imply, but grows inland as far east as Glacier National Park, Montana. Generally, it is a small tree, 7–13 meters in height and 5–10 cm in diameter. The crown is large and conical. Commonly, however, it is contorted with the main stem and some of the lower limbs growing close to the ground producing numerous adventitious roots resulting in a complex and dense interwoven thicket of growth. The tree is usually associated with deep, rich, moist soils near streams and lakes. It is an understory tree commonly found with Douglas fir, Western hemlock, Western red cedar and Western larch.

The inner bark of this remarkable little tree is the primary source of taxol. Taxol is a highly derivatized terpenoid having the structure indicated above, and has shown remarkable promise as an anti-tumor agent especially in breast and ovarian cancers. Unfortunately, at the present time, the supplies of taxol are inadequate to meet the current or projected demands. Taxol is only currently available from extract from the bark of yew trees. The inadequate supply of taxol is reflected in its current market price which is $6000.00 per gram. Thus, it is essential to understand how, where, and when, taxol is biosynthesized in the tree and the factors that affect its biosynthesis.

It is likely that many factors influence the production of taxol by Pacific yew. These include not only various environmental factors such as temperature and moisture level, but the genetic background of the tree itself. Also, plants are commonly hosts to a multitude of microbes including parasites, symbionts, endophytes, epiphytes, and mycorrhizal fungi. These organisms may also influence the production of secondary plant metabolites such as phytoalexins, whose presence can be triggered by elicitors from microbes. Such microbes may catabolize or derivatize plant compounds.

These and other reasons prompted the present inventors to devise an "in vitro" system of taxol production (see related U.S. patent application Ser. No. 07/845,097, filed Mar. 3, 1992. The system utilizes isotopic precursors of taxol, an optimized environment and the appropriate plant parts where taxol is synthesized. The result was an "in vitro" system of taxol synthesis from the most productive tissue portions of the Pacific yew tree.

However, the above in vitro synthesis described in related application Ser. No. 07/845,097 has certain limitations. The source of taxol production, the Pacific yew, is a relatively rare tree, and there is concern that the supply of taxol is not adequate to meet the demand.

Moreover, other methods, including total chemical synthesis, and derivatization of baccatin to yield taxotere are both inadequate. The chemical synthesis methods are multi-stepped and non-economically feasible while the taxane derivatization method utilizes a taxane isolated from yew needles.

Clearly, a microbial source of taxol would be preferable if it could be easily grown, would produce taxol (or a related taxane), and utilize the enormous U.S. biotechnology industry fermentation capabilities.

SUMMARY OF THE INVENTION

Accordingly, it is an object of the present invention to provide an improved process for producing taxol, using a taxol producing microbe followed by separation of taxol from the growth medium and/or microbe.

In a further embodiment of the invention, there is provided a radioactive labelled taxol product and methods for use of the radioactive labelled taxol. The labelled taxol can be produced by use of a labelled precursor as described herein. Radiolabelled taxol is a new compound for the present invention and related application Ser. No. 07/845,097 (which produces the labelled taxol by a different process). Because of its radiolabel, it and its derivatives can be identified in the mammal body so one can determine how it functions as an antileukemic and antitumor agent. The taxol may be labelled with any label (stable or unstable) including $^{14}C$, $^{13}C$, tritium ($^3H$) or with $^{15}N$.

STATEMENT OF THE INVENTION

The present invention provides an improved process for producing taxol, which uses a taxol producing microorganism followed by separation of taxol from the growth medium and/or microorganism. One aspect of the invention is a method for isolating a microorganism which produces a taxane, which comprises the following steps:

(a) obtaining tissue fragments from a tree of the Genus Taxus, (b) placing said tissue fragments on agar medium until fungal growth occurs e.g., about 2–5 days, (c) placing fungal hyphae from said fungal growth on mycological agar, and replacing said fungal hyphae on said mycological agar if necessary, until a culture in pure form is obtained, (d) transferring said fungal hyphae to a fungal lab growth medium, with subsequent growth of the fungal culture, (e) removing at least a portion of the culture media containing the fungal culture, thoroughly grinding the mycelium, and adding an organic solvent to the mixture, (f) obtaining a chromatograph of said fungal culture in said solvent, (g) checking the solution for the taxane reaction, e.g., with vanillin-sulfuric acid spray, and comparing the chromatograph with one or more taxane standards such as taxol, baccatin, cephalomannine, and optionally (h) discarding the cultures which do not produce taxol. Optionally, the cultures which do not produce taxol may be preserved for additional testing.

Preferred members of the Genus Taxus are *Taxus brevifolia, Taxus baccata, Taxus cuspiduta, Taxus canadensis*, and *Taxus floridana*. Particularly preferred is *Taxus brevifolia*.

The present invention further provides a class of microbes which have taxol-producing characteristics. Montana BA, the characteristics of which are described in detail below, is representative of such microbes. Ten additional taxol producing microbes are also disclosed. The microbes according to the present invention produce taxol in culture. Preferred taxol-producing microbes are fungi, and particularly preferred is a taxol producing fungi isolated from a yew tree. Even more preferred is a fungus designated Montana BA. The present invention provides the major discovery of microbes which will produce taxol. The invention covers any microbe which has taxol producing characteristics. The specific microbes described are considered representative only.

Also, the present invention comprises a taxane composition obtained by culturing a microbe. Preferred is a taxane of the species taxol. Particularly preferred is a taxol composition produced by a microbe, e.g., a fungus having the taxol-producing characteristics of Montana BA.

In another aspect, the present invention provides a radiolabelled taxane composition obtained by culturing a microbe. Preferred is a radiolabelled taxol composition produced by a microbe which is a fungus. Even more preferred is a labelled composition produced by a microbe which is a fungus having the characteristics of Montana BA. Particularly preferred labels are $^{14}C$, $^{13}C$, $^{3}H$, or $^{15}N$.

The present invention provides an improved method for producing a bulk pharmaceutical composition, which contains a pharmaceutically effective amount of a taxol composition, combined with one or more pharmaceutically acceptable inert or physiologically active diluents or adjuvants.

Also provided is a pharmaceutical composition, which contains a pharmaceutically effective amount of a radiolabelled taxol composition, as described above, combined with one or more pharmaceutically acceptable inert or physiologically active diluents or adjuvants.

Moreover, the present invention includes a method for the treatment of leukemia or tumors which comprises administering a pharmaceutical composition containing taxol as described above.

In yet another aspect, the present invention provides a method for producing a taxane, which comprises a) exposing a taxane producing microbe according to the present invention as described above to a nutrient media capable of supporting growth of the microbe, b) providing culturing conditions for the media containing the microbe, which conditions are capable of producing growth and reproduction of the microbe, and c) isolating or concentrating the desired taxane from said culture media or said microbe.

Preferred is a method for producing a taxol composition wherein the microbe has the taxol-producing characteristics of Montana BA. More preferred is such a method wherein the microbe is a taxol producing fungi. Further preferred is a method wherein the microbe is isolated from a yew tree.

Also preferred is a method for producing a taxane, as described above, wherein the nutrient media comprises benzoic acid, a benzoic acid metabolite precursor, or a salt of benzoic acid, such as sodium benzoate. Particularly preferred is a method as described above for producing the taxane, wherein the taxane is taxol.

A preferred method for producing a taxane comprises a) exposing a taxol producing microbe to a nutrient media capable of supporting growth of said microbe, b) providing culturing conditions for said media containing said microbe, which are capable of producing growth and reproduction of said microbe, and c) isolating or concentrating said taxane from said culture media or said microbe.

Also preferred is a method for producing a taxane which comprises a) exposing a taxol producing microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxane from said culture media or said microbe.

In another preferred aspect of the present invention provides a method for producing a taxol which comprises a) exposing a taxol producing microbe of the invention to a nutrient media capable of supporting growth of said microbe, wherein said media contains benzoic acid, b) providing culturing conditions for said media containing said microbe, which conditions are capable of producing growth and reproduction of said microbe, and c) isolating or concentrating said taxol from said culture media or said microbe.

DESCRIPTION OF THE INVENTION

Figure 1:
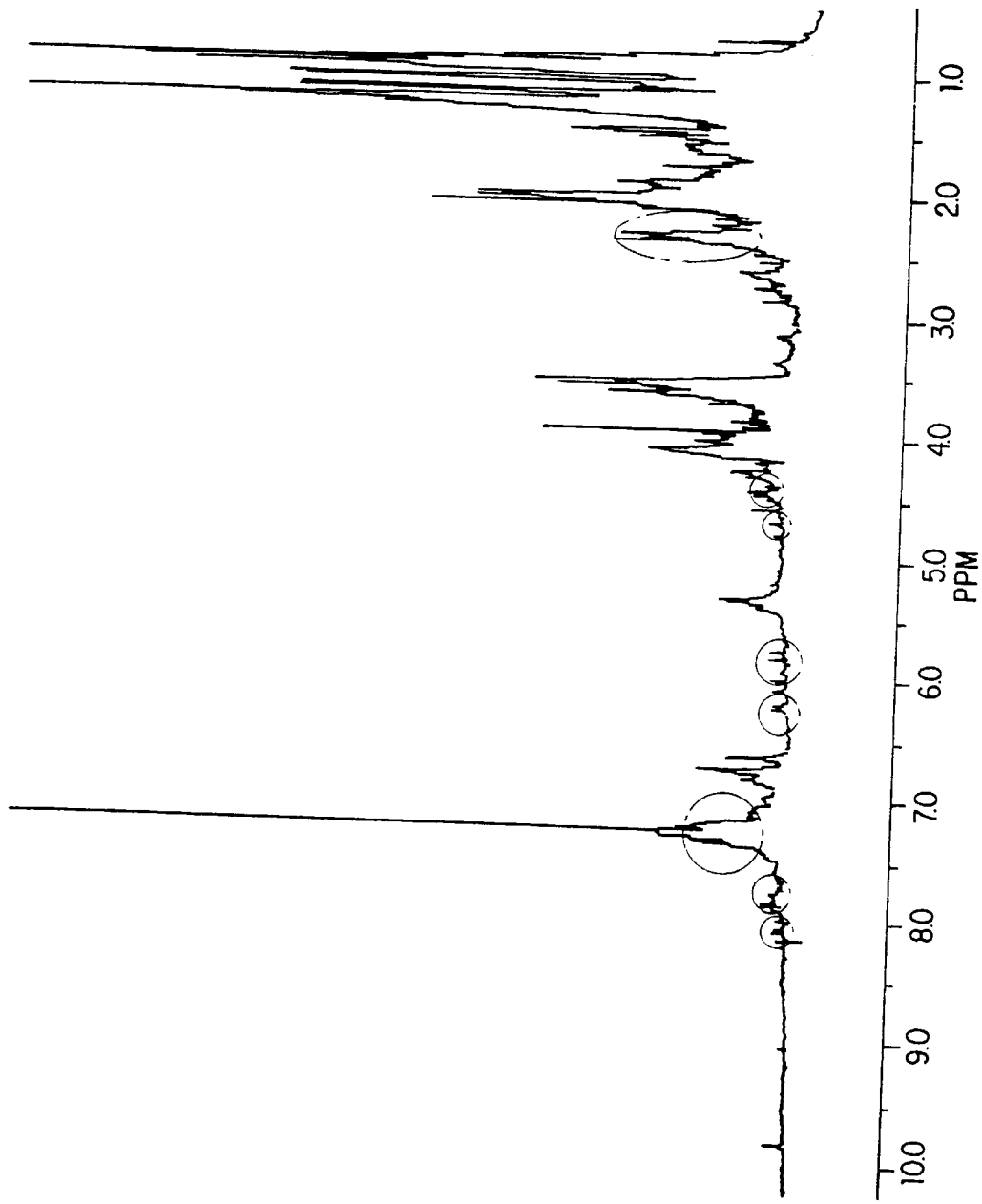
FIG. 1 shows the NMR spectrum of a semi-purified culture extract from Montana BA fungus.

All land plants serve as life support systems to a host of microbes. The microbes exist as parasites, saprophytes, endophytes, symbionts or mycorrhizae. On occasion, there may be intergeneric exchange of genetic information between one or more of these organisms and its hosts, or vise versa. With the former case, it is well documented that certain species of agrobacteria are capable of genetically transforming their host plants via either the Ri or Ti plasmids. The result is that a genetically altered plant is formed that has one or more characteristics of the agrobacterium.

Numerous cases are known in which all phytohormones, known throughout the plant kingdom, are also produced by one or more plant parasitic bacteria or fungi. These include indole acetic acid, the gibberillins, some cytokinins, abscissic acid and ethylene. Recently, the present applicants have also shown that certain terpenoids that were originally thought to be exclusively higher plant associated compounds, are also produced by a plant pathogenic fungus (See, Bunkers et al., "Production of Petasol", Mycol. Res 95, (3); 347–351 (1991)).

Thus, while there is no published evidence that taxol could or would be produced by any microorganism, the present applicants explored the microorganism possibility. The inventors suspected that taxol (taxanes) may be produced by one or more microbes associated with the yew tree.

The basis for this concept was that microbes may exist which will produce taxol because of a possible genetic exchange which may have previously occurred, either between the microbe(s) (as original source of taxol) or yew (as original source of taxol). The net result would be the most desirable case of possessing one or more microbes which could be placed in fermenters to produce taxol.

The present invention provides a method for locating and isolating microorganisms which produce taxol, and provides specific examples where such taxol producing organisms are found. Other microorganisms associated with the yew or related trees, which produce taxol or related taxanes, may be isolated using the present method. Therefore, the present invention is considered to be inclusive of all such microbes, or any pharmaceutical.

One method of the invention involves finding, isolating and characterizing one or more microbes from yew forests or elsewhere which produce taxol (taxanes). One place to focus the search for such an organism was in one or more locations which have naturally supported the growth of yew trees for centuries.

After locating the yew tree, the following general method is followed to isolate microbes which produce taxol. Small stems were cut from the yew tree, treated with 70% ethanol as a disinfectant and then, with a sterile blade, removing the outer bark. Pieces of the inner bark of the stem, which is enriched with taxol (Wani's paper), are then placed on agar medium (water agar) until fungal growth occurs after 2–5 days. Then, tips of the fungal hyphae are removed from the water agar and subsequently placed on mycological agar. The culture is obtained in a pure form as judged by its behavior on the plate. Lab contaminants seldom occur due to the rigor of the aseptic technique which was used.

Once the organism is obtained in a pure form it is ultimately transferred to one or more lab media. In this case the modified M-1-D medium (Table 1, below) with yeast extract is used to support the growth of the microbe. Alternatively, (Table 2, below) another medium which resembles the soluble sugars (quantity and quality) of the yew bark, plus a mixture of amino acids (or critical amino acids and another nitrogen source, such as ammonium salts), Na benzoate and acetate are included.

TABLE 1

| Modified M-I-D Media (Filner) | | |
|---|---|---|
| | | g/l |
| Ca(NO$_3$)$_2$ | 1.20 mM | 0.28 |
| KNO$_3$ | 0.79 mM | 0.08 |
| KCl | 0.87 mM | 0.06 |
| MgSO$_4$ | 3.00 mM | 0.36 |
| NaH$_2$PO$_4$—H$_2$O | 0.14 mM | 0.02 |
| Sucrose | 87.60 mM | 30.00 |
| Ammonium Tartrate | 27.10 mM | 5.00 |
| | | mg/l |
| FeCl$_3$—6H$_2$O | 7.4 μM | 2.0 |
| MnSO$_4$ | 30.0 μM | 5.0 |
| ZnSO$_4$—7H$_2$O | 8.7 μM | 2.5 |
| H$_3$BO$_3$ | 2.2 μM | 1.4 |
| KI | 4.5 μM | 0.7 |

TABLE 1-continued

Modified M-I-D Media (Filner)

pH 5.5 with 0.1M MCl
0.25 g Yeast Extract*

*Or omit the Yeast and supplement with:
Stock Biotin 0.5 mg/ml
Stock Thiamine 0.5 mg/ml in 40% aq. EtoH
Stock Inositol 5 mg/ml
Use 2 ml/l of broth

TABLE 2

Taxol Microbial Culture Medium

|  | Grams/Liter | |
| --- | --- | --- |
| glucose | 1 | |
| fructose | 3 | |
| sucrose | 6 | |
| KHPO$_4$—KH$_2$PO$_4$ | 1 ml of 1M pH 6.8 | |
| MgSO$_4$ | .36 | |
| Ca(NO$_3$)$_2$H$_2$O | .65 | |
| Yeast extract | 0.5 | g |
| Ca(NO$_3$)$_2$ | 1.0 | mg |
| ZnSO$_4$ | 2.5 | |
| MnCl$_2$ | .5 | |
| FeCl$_2$ | 2.0 | |
| leucine | 0.1 | mM |
| phenylalanine | 0.01 | mM |
| NaAc | 1.0 | mM |

The incubation of the fungus is carried out at 25° C. (in 100 ml of medium in a 250 ml flask, for example) under still conditions (occasionally shake periodically—every other day, for example) for 3 weeks. At the end of the incubation period the fluid (media) is decanted and the mycelium is thoroughly ground (disrupted) at maximum speed in a Sorvall Ominimixer for 30 sec. Then, an equal volume of chloroform methanol solution 10:1 v/v is added to the medium and ground fungal mycelial solutions. The chloroform layer (bottom) is removed in a separatory funnel. The process may be twice repeated. Ultimately, the chloroform layers are collected together and subjected to flash evaporation under a vacuum at 35–40° C. until dry.

A portion of the residue is then chromatographed on a 5×10 cm plate of silica gel in solvent P (below) (Merck silica gel 0.25 mm). Authentic standards of taxol, baccatin, and cephalomannine are also chromatographed for comparison.

The aqueous layer is lyophilized and thoroughly extracted with chloroform methanol 1:1. When evaporated, it is chromatographed in the same manner as above.

The standard solvents used in the chromatographic procedures are:

A) chloroform/methanol 7:1 V/V
B) chloroform/acetonitrile 7:3 V/V
C) ethyl acetate/isopropanol 95:5 V/V
D) methylene dichloride/tetrahydrofuran 6:2 V/V.

The taxanes (taxol, baccatin, cephalomannine) all absorb short wave UV light (254 angstroms) and react with the vanillin-sulfuric acid spray (see, Cardellina, J. Liquid Chromatography 14: p 6659–665 (1991) to produce an intense blue coloration fading to gray then turning brown after 24 hours.

Each fungus culture was treated in the same manner. At least 50 fungi and 10 bacteria were isolated from yew roots, needles, stems, or fruits and tested. Samples of the extract from each organism were subjected to initial screening by thin layer chromatography (TLC) in solvent A.

A few microbes appeared promising after the initial screening. That is, their extract produced a blue spot at R$_f$ 0.75–0.81 in solvent A (same as taxol). These microbes were fungi and one later identified as *Cladosporium macrocarpum*, was further checked for taxol by other methods—but without success. A strain of fungus, designated Montana BA, exhibited several important absorbances in HNMR consistent with the spectrum of taxol (see FIG. 1). Therefore, this culture held promise for taxol production and was studied further. The following are descriptions of the fungus and taxane production.

(1) Montana BA—rapidly growing on potato dextrose agar, most hyphae with growth oppressed to agar surface, no apparent fruiting structures, beige coloration of hyphae. (Culture on deposit with the Centraal Bureau voor Schimmelcultures under the terms of the Budapest Treaty as Accession No. CBS 279.92).

(2) Evidence for taxol (taxane) production
    (a) The fungus was grown in both M-1-D and Taxol Microbial culture medium (2 liters) for 3 weeks at 25° C. with only periodic shaking. The medium and the grown mycelium were extracted with chloroform: MeOH 10:1 v/v.

After evaporation of the chloroform:MeOH the residue was taken up in 0.5ml of CHCl$_3$ MeOH 10:1 v/v and subjected to preparative TLC in solvent B on Merck plates 0.5 mm (20×20). A band at R$_F$ 0.47–0.50 that had slight UV (254 angstroms) absorbance and gave a slight reaction with the vanillin sulfuric acid spray was scraped from the plate and eluted with acetonitrile. Only the extreme edge is sprayed, unadulterated material is scraped and eluted.

Figure 2:
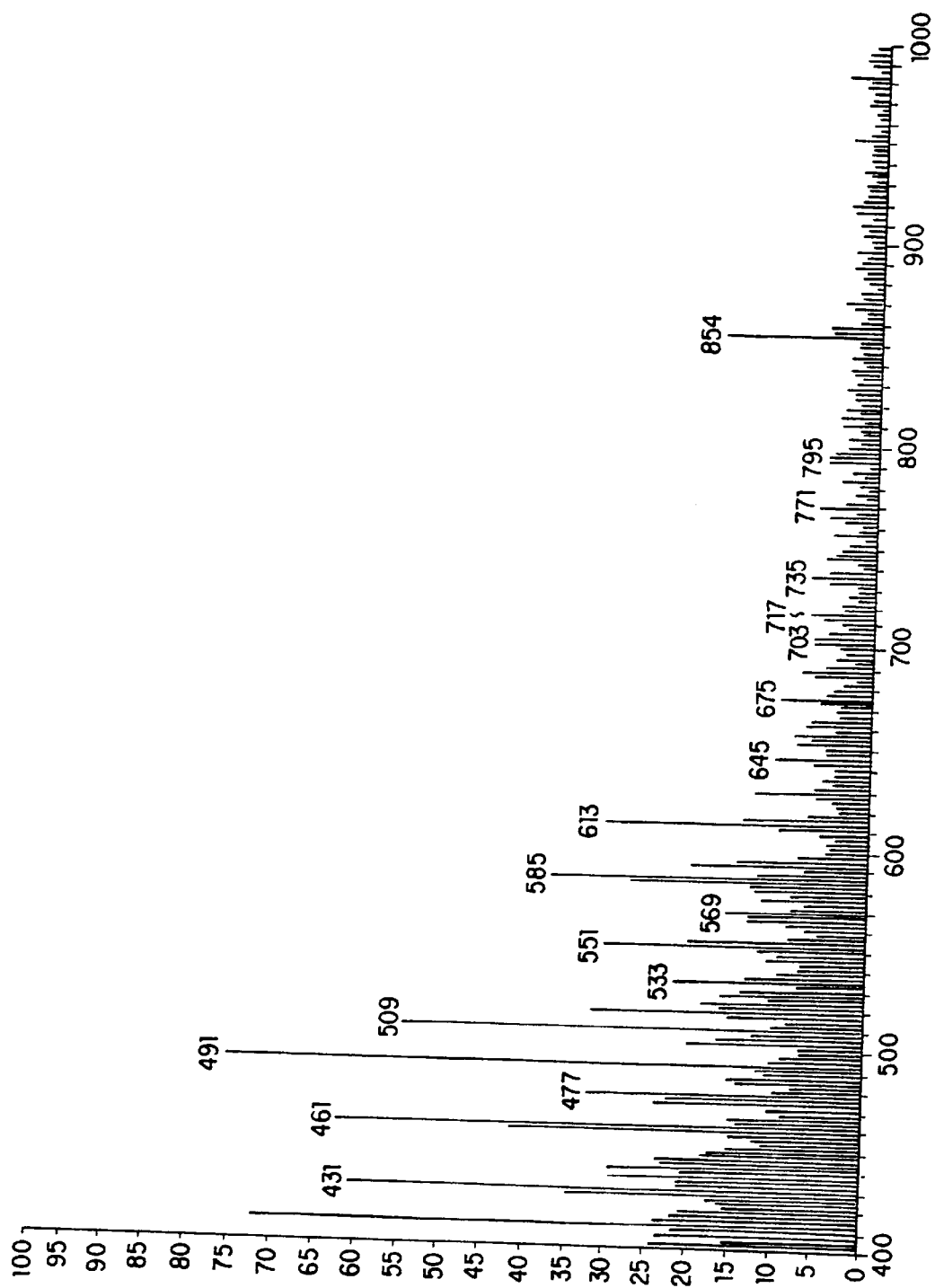
FIG. 2 shows a FAB mass spectrum of taxol obtained by culturing the Montana BA fungus.

Further chromatography was done in solvent A in TLC (precleaned plates with the same solvent). The "taxol" band was eluted and subjected to spectroscopy. This band had the same FAB mass spectrum as authentic taxol with an M$^{+1}$ at 854 and prominent peaks at 491, 509 and 613 (see FIG. 2).

The UV spectrum of the compound had an absorption maximum at 273 nm which is identical to authentic taxol (see Wani et al). The NMR spectrum of the semi-purified compound possessed all of the major absorbances of authentic taxol (FIG. 1).

In addition, the R$_F$ values for the taxol preparation from the fungus "Montana BA" was identical to authentic taxol (see Table 3 below).

TABLE 3

Comparative R$_F$ values of fungal taxol to authentic taxol and baccatin

Solvent System:

| | CHCl$_3$/MeOH 78:1 v/v |
| --- | --- |
| taxol | .81 |
| fungal | .81 |
| baccatin | .75 |
| fungal baccatin | .75 |
| | CHCl$_3$ Acetonitrile 7:3 v/v |
| taxol | .47 |
| fungal taxol | .47 |
| baccatin | .50 |
| fungal baccatin | .50 |
| | Ethyl acetate isopropanol 95:5 v/v |
| taxol | .63 |
| fungal taxol | .63 |
| baccatin | .58 |
| fungal baccatin | .58 |

TABLE 3-continued

Comparative $R_F$ values of fungal taxol to authentic taxol and baccatin

Solvent System:

| | $Ch_2Cl_2$ Tetrahydrofuran 6:2 v/v |
|---|---|
| taxol | .75 |
| fungal taxol | .75 |
| baccatin | .67 |
| fungal baccatin | .67 |

It is also to be noted that the compound "baccatin", a taxane related to taxol, also appeared in the fungal extract. It, along with taxol, yielded the same intense blue color reaction and the same UV (254) absorption properties as the authentic compounds. It also had the same $R_F$s as authentic baccatin (Table 3).

TABLE 4

Enhanced Taxol Microbial Culture Medium

| | Grams/Liter |
|---|---|
| glucose | 1 |
| fructose | 3 |
| sucrose | 6 |
| KHPO—$KH_2PO_4$ | 1 ml of 1M pH 6.8 |
| $MgSO_4$ | .36 |
| $Ca(NO_3)_2H_2O$ | .65 |
| Yeast extract | 0.5 |
| $Ca(NO_3)_2$ | 1.0 mg |
| $ZnSO_4$ | 2.5 |
| $MnCl_2$ | 0.5 |
| $FeCl_2$ | 2.0 |
| phenylalanine | 5.0 mg |
| NaAc | 1.0 g |
| Sodium Benzoate | 10 mg–100 mg |

The amount of taxol per liter (3 wk old culture) is estimated at about 1–2 µg. Baccatin appears at a level of 0.5–1 µg/liter.

The taxonomy and properties of the microbe revealed a fungus of the family *Fungi imperfecti* (or alternatively called the family Hyphomyces). The genus was determined to be Taxomyces and the species was named *andreanae*.

*T. andreanae* (Montana BA) forms the bulbil or sterile cell masses which appear to be unique structures.

Type species: *Taxomyces andreanae* Strobel, Stierle, & Hess.

Holotypus: Based on material taken from the bark of *Taxus brevifolia* Nutt. infested living bark samples, agar slants containing the type are deposited with the Montana State University (MSU) mycological collection, D. E. Mathre, Department of Plant Pathology, Montana State University—col. no. 738. Duplicate cultures are deposited at the CBS, Baarn, Holland 25 culture 279.92.

A pure culture species was obtained of Montana BA which was named *Taxomyces andreanae* S1. Two further fungal cultures, other than Montana BA, which produced taxanes were obtained from the above screening. Their characteristics revealed them to be of the same genus and species, but to have slightly different properties in that each strain differed in hyphal morphology and growth. These microbes were isolated to pure culture form and given the names *Taxomyces andreanae* 52 and *Taxomyces andreanae* 53, respectively. Further details are presented below in the experimental section.

(b) To dispel the notion that the taxol isolated from the culture medium might be occurring as a result of the fungus's previous association with the yew tree, the fungus "plugs" used to inoculate the medium were exhaustively extracted and the residue chromatographed. There was no evidence of taxol.

(c) In order to be assured that taxol is produced "de novo" by the fungus, the fungus was incubated for 3 weeks in two 500 ml cultures of Taxol Microbial Culture medium and added 100 µCi of NaAC-1- $^{14}C$ (54 mCi/mole) plus 125 µCi of mixed amino acids 1.75 mCi/mg. Both the taxol and baccatin areas on the preparative TLC's were isolated and then subjected on 2 plates to 3 dimensional TLC (20×20 plate—25 mm layer) along with (co-chromatography) authentic taxol and baccatin. The UV absorbing spot was removed by scraping and counted by liquid scintillation counting methods. The results show that the area on the plates having radioactivity was identical to the UV absorbing spot. This was true on both taxol and baccatin. This test assures that both baccatin and taxol were synthesized 'de novo' by the fungus.

Throughout the course of the taxol microbial study, a means of determining the cytotoxicity of the culture extracts and various column fractions to facilitate bioassay guided fractionation was needed. Ferrigni et al., J. Nat. Prod. 45, 679 (1982); and Ferrigni et al., J. Nat. Prod. 47, 347 (1984), suggested that a simple brine shrimp assay provided a reasonable facsimile of the standard anticancer assays. Those authors were able to isolate the antileukemic principles from the seeds of *Euphorbia lagascae* Spreng using a fractionation scheme guided by brine shrimp and potato disc assays. Several studies have demonstrated good correlation between brine shrimp lethality and cytotoxicity.

The brine shrimp bioassay is a simple test. Brine shrimp are hatched in Instant Ocean dissolved in tap water, which generates a solution that approximates the constituents of sea water. The test material is handled according to its polarity and purity. Crude culture residues are tested at 10 mg, simply dissolved in the saline water used to rear the brine shrimp. The test material is dissolved in 2 ml of salt water, and an additional 2 ml of salt water containing the brine shrimp is added. The brine shrimp are counted, then recounted at various time intervals. Toxicity is determined by the number of brine shrimp deaths which result from the test material, relative to a control of saline water, and a control of authentic taxol.

Biological activity of the Montana BA extract showed positive α-action (antitubulin) activity which is the comparable activity observed for authentic taxol (see references). Other biological activities observed were a positive brine shrimp test.

The members of the genus/species *Taxomyces andreanae* were cultivated with labeled nutrients to show definitively that the microbes produced taxanes. It was determined that the addition of benzoic acid to the culture medium increased the amount of taxol and other taxanes.

The present invention is directed to any microbe, especially fungi, which have taxane producing characteristics, especially as described in the present invention, irrespective of their source. Such microbes are those which can produce taxol by the NMR spectrum of FIG. 1, the FAB mass spectrum of FIG. 2, the SEMS of FIGS. 4, 5 and 6 and the TEM of FIGS. 8 and 9.

In another aspect of the invention, referred to above, an appropriately labelled precursor is used to produce labelled taxol. $^{14}C$-phenylalanine is the preferred amino acid precursor, for $^{14}C$-taxol production. However, as in the above example, Na acetate-1-$^{14}C$ can be used because of its relatively low price and ability to label taxol uniformly.

The taxanes, e.g., taxol, or radiolabelled taxanes produced according to the present invention, can also be provided as a pharmaceutical composition in combination with one or more pharmaceutically acceptable inert or physiologically active diluents or adjuvants. These compositions may be prepared in any form appropriate for the administration route desired. The parenteral route and especially the intravenous route are preferred methods of administration. Compositions for parenteral administration may be aqueous or nonaqueous sterile solutions, suspension or emulsions. Propylene glycol, vegetable oils, injectable organic esters and the like, may be used as solvents or vehicles. The compositions may also contain adjuvants, wetting agents, emulsifiers or dispersants.

The compositions may also be in the form of sterile solid solutions which may be dissolved or dispersed in sterile water or any injectable sterile medium. The pharmaceutical compositions may be particularly used in the treatment of acute leukemia and solid tumors at doses known to the art, but generally in the range of between one and two milligrams per kilogram of body weight by the intravenous route for an adult. The pharmaceutical compositions should contain about 0.001 to 1.0 wt. % of effective ingredient and administered in dosage amounts known to the art for taxol.

The above microbial culture method allows for bulk compositions comprising amounts of taxanes, i.e., taxol, in bulk quantities not previously available. Previously, only small amounts of taxol, e.g., only a few hundred milligrams, have been available from extraction and other methods.

An example of a taxol microbial culture medium is set forth below in table 5.

TABLE 5

Taxol Microbial Culture Medium
(high sugars)

|  | 8/liter |
| --- | --- |
| glucose | 1 |
| fructose | 3 |
| sucrose | 6 |
| Na acetate | 1 |
| casein amino acids | 0.5 |
| $KH_2PO_4$ | pH 6.8    1 ml of 1M |

|  | mg/liter |
| --- | --- |
| vitamins |  |
| thiamine | 1 |
| biotin | 1 |
| pyridoxal | 1 |
| calcium pantothenate | 1 |
| sodium benzoate | 10–100 |
| $MgSO_4$ | 3.6 |
| $Ca(NO_3)_2$ | 6.5 |
| $Ca(NO_3)_2$ | 1 |
| $ZnSO_4$ | 2.5 |
| $MnCl_2$ | 5 |
| $FeCl_2$ | 2 |

TABLE 6

Growth and bulbil formation of *Taxomyces andreanae* on various tree species normally growing in the vicinity of *Taxus brevifolia*. All observations were recorded 1 week after inoculation with a 1.0 × 1.0 agar block supporting fungal growth.

| Plant Species | Av growth from edge of agar block (cm) | | Formation of bulbils* | |
| --- | --- | --- | --- | --- |
| | Twigs/ leaves | Bark | Twigs/ leaves | Bark |
| *Taxus brevifolia* Nutt. Pacific Yew | 2.0 | 0.25–0.5 | heavy | heavy |
| *Betula nigra* L. River Birch | 1.0 | 0.75 | heavy | moderate |
| *Pinus monticola* Dougl. Western white, pine | 0.1 | 0.2 | light | light |
| *Tsuga heterophylia* Rafn Sarg. Western Hemlock | 0.0 | 0.1 | none | none |
| *Pseudotsuga taxifolia* (Poir) Britt. Douglas fir | 0.1 | 0 | none | none |
| *Thuja plicata* Donn Western Red Cedar | 0.5 | 0.5 | light to moderate | heavy |
| *Picea engelmanni* Parry ex Engelm. Engelmann spruce | 0.1 | 0 | moderate | none |
| *Larix occidentalis* Nutt. Western larch | 0 | 0 | none | none |

*Bulbil formation is given in terms of heavy (completely covering the area where mycelium is growing) to moderate, to light (little or sparse bulbil formation).

The fungi according to the present invention, when grown in a defined medium, use sodium benzoate 10–100 mgs/liter to recover the taxol from the medium. The fungi are preferably maintained as an inoculum source in a freshly prepared malt agar (100 mgs of benzoate/liter). The fungi do not grow well on shake culture. The optimal fungal growth occurs on bactosoytone 5–7 grams/liter (instead of peptone include the essential amino acids and fructose and glucose). With 10 grams sucrose, together with benzoate, vitamins and minerals as per Taxol Microbial culture medium. To further confirm the presence of taxol and baccatin in fungal preparations and extract, a culture of *T. andreanae* was prepared by $CHCl_3$/MeOH extraction, prepared TLC on $CHCl_3$/acetonitrile 7:3 v/v followed by elution of a 1 centimeter wide area at $R_F$ 0.18–0.25. Then the residue was subjected to a micropore HPLC separation from optimum sensitivity. The study was conducted on LC/MS using a reverse phase column (1 mm)×150 mm×5 μm particles with an Isocratic mobile phase consisting of 65 percent acetonitrile/35 percent 2 mM ammonium acetate at a flow rate of 50 microliters/minute. Subsequent analysis of two microliters of the sample prepared from 100 microliters of the dissolved sample prepared from 100 microliters of the dissolved sample yielded a peak with the retention time identical to taxol (7.85 minutes) and 6.4 minutes consistent with the pseudomolecular ion $(M+NH_4)^+$ baccatin III.

Figure 3:
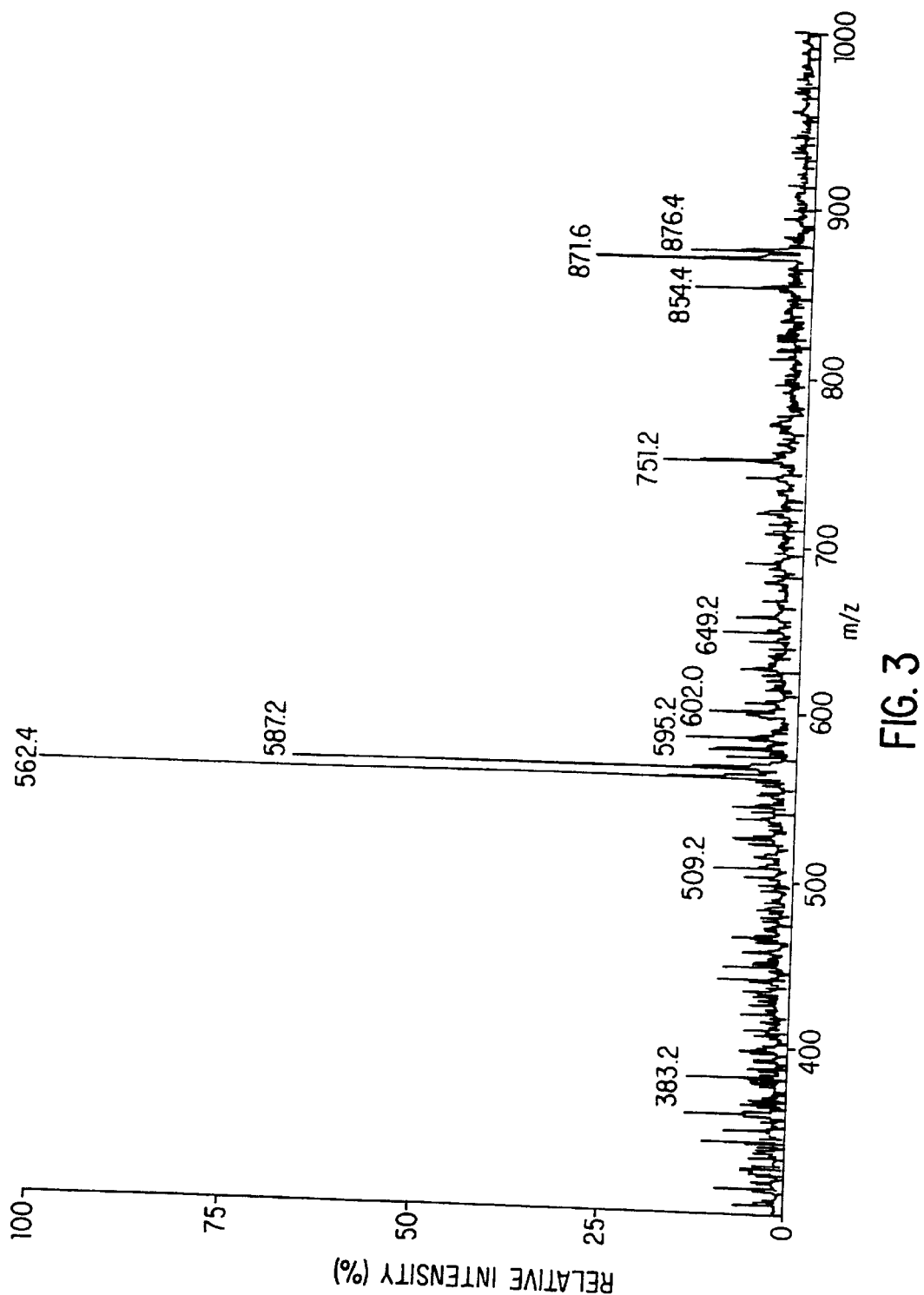
FIG. 3 shows a flow injection ion spray mass spectrum of TLC fraction RF 0.18 of fungus extract after injections of diluent wherein the low intensity ions consistent with taxol are m/z 854 and 871.

FIG. 3 illustrates the mass spectrum of the taxol eluting peak at 854–871 consistent with taxol. The amount of taxol produced in this particular medium is approximately 1 microgram/liter of the medium.

This does not represent endogenous taxol from the yew tree for several reasons. Radiolabeling experiments with phenylalanine, sodium benzoate or acetate $^{14}$C as precursors yields radiolabelled taxol. Accordingly, the experiments clearly show that the taxol is being synthesized.

To further describe the *Taxomyces andreanae* microbe, the following detailed examples are provided.

EXAMPLE 1

*Taxomyces andreanae* is a novel endophytic fungus associated with the inner bark of *Taxus brevifolia* Nutt. (Pacific Yew). This fungus has small hyphae which average 1.2 μm in diameter. It characteristically forms clumps of loosely constructed cells (bulbil-like) . These clumps of various shapes and sizes typically range from about 5×5 to 16×30 μm in diameter and length. The cells in these clumps average about 1.5×2.5 μm and appear to be loosely packed in the bulbi and are incapable of germination. This fungi grows rapidly on many common laboratory media, covering the plates with its mycelium in three or four days. It lacks clamp connections and dolipore septations. Its telemorph is unknown. The *Taxomyces andreanae* is a endophytic hyphomycete, isolated exclusively from the inner bark on small limbs of a specific yew tree in northern Montana.

The fungus species were isolated from the upper limbs of a shrub-like Pacific yew tree growing as undercover in a mature undisturbed cedar forest in Flathead County, Montana. Small limbs (0.5–1.0 centimeter) were surface treated with 70 percent ethanol. The outer bark was peeled back and pieces of the white inner barks (phloem/cambium) were aseptically removed and placed on H$_2$O agar. Hyphal tips of fungi growing from the pieces of the plant were placed on mycological agar and fungal growth was enhanced. The growth pattern of the fungus was studied on other plant species. Leaf, stem, and bark samples of various plant species growing near the tree from which this fungus was obtained were collected near the Hungry Horse dam site in the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco), e. t., potato dextrose broth agar, nutrient agar, oatmeal agar, cornmeal agar, lima bean agar, water agar, and malt agar.

EXAMPLE 2

Agar blocks having mycelia and bulbil-like structures were fixed and dehydrated as for transmission and scanning electron microscopy (SEM) (FIGS. 6, 7, 8, and 9) . For SEM, the material was then critical point dried, gold coated and sputter coated, and observed with a JEOL 840A scanning electron microscope. Fungal structures were measured on SEM micrographs after critical point drying of tissues.

This drying procedure caused some shrinkage of biological structures (about 10 percent) which means that they were probably slightly larger, and the clumps of cells more tightly packed than in the living state.

EXAMPLE 3

Taxonomic Treatment and Description *Taxomyces andreanae* S1: Strobel, Stierle and Hess gen. et sp. nov. (FIGS. 4–9). A pure culture species was obtained of Montana BA which was named *Taxomyces andreanae* S1. This microbe producing taxane was obtained from the above screening. Its structures are described as follows.

Fungus endophyticus e cortice interiora Taxo brevifolo Nutt.; hyphae dimporphae—parvae 1.25 μm et magnae ca 3.75 μm latae et longae; bulbilus cellularum ca 1.25×2.5 μm et laxe continguus et apparenter non germinans; mycelium celiter crescens, hyphis fibulis nullis et doliporis septis nullis; telemorphus ignotus.

Figure 4:
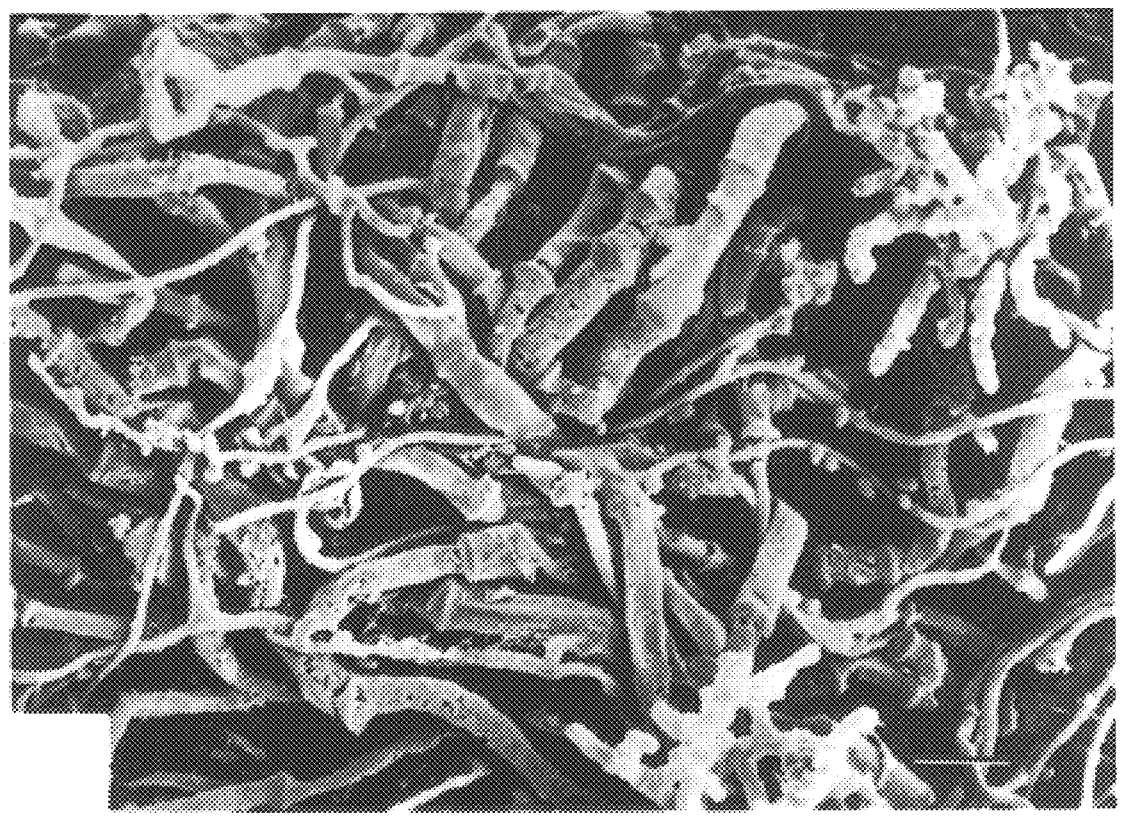
FIG. 4 shows a scanning electron micrograph of hyphae and fructigenous hyphae of *T. andreanae*; Bar equals 10 μm.
Figure 5:
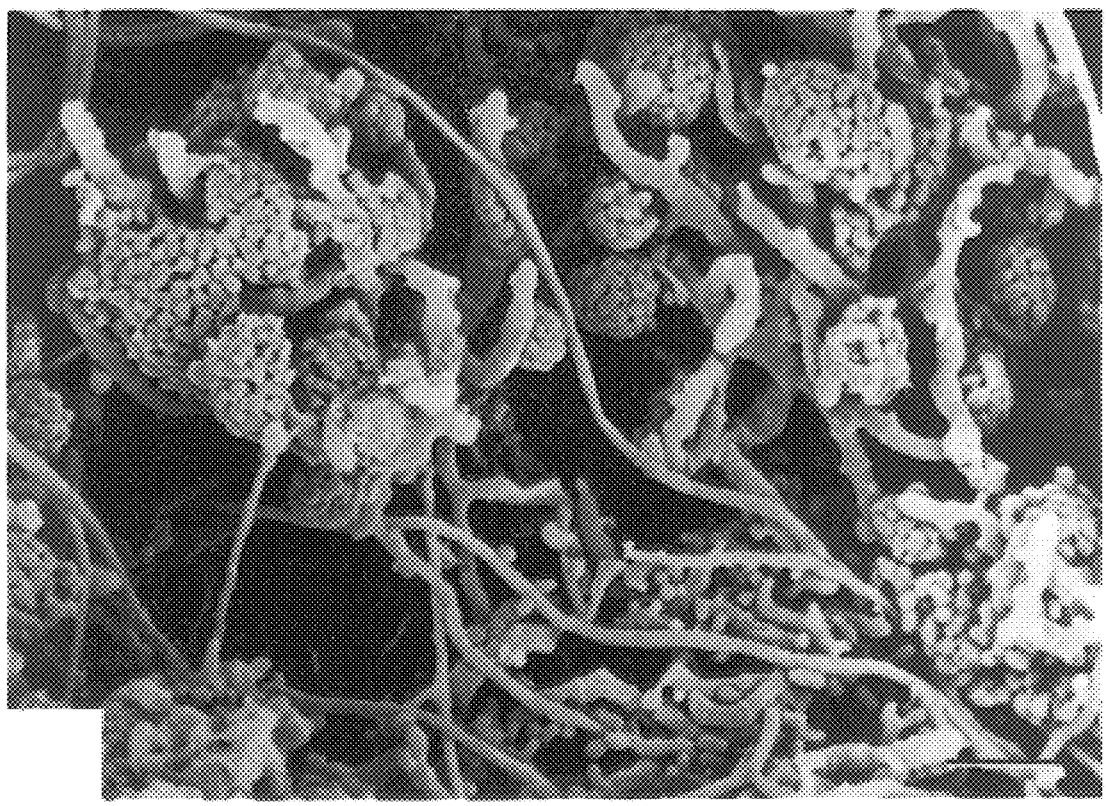
FIG. 5 shows a scanning electron micrograph of a series of various shape bulbils of *T. andreanae*; Bar=10 μm.

Mycelium superficial, composed of a network of highly branched, septate, usually hyaline, smooth walled hyphae. Smaller hyphal cells average 1.25 μm in diameter. Larger cells average 3.75 μm in diameter (FIGS. 4–5). Cells are budded from fructigenous hyphae forming clumps which vary enormously in shape from spherical to ovoid to longiform and in size from 5×5 μm in length (for elongate bulbils) . Bulbil cells remaining colorless. The cells seem to be loosely packed in the bulbil and are ovoid ca. 1.5×2.5 μm and are never observed to germinate.

Figure 6:
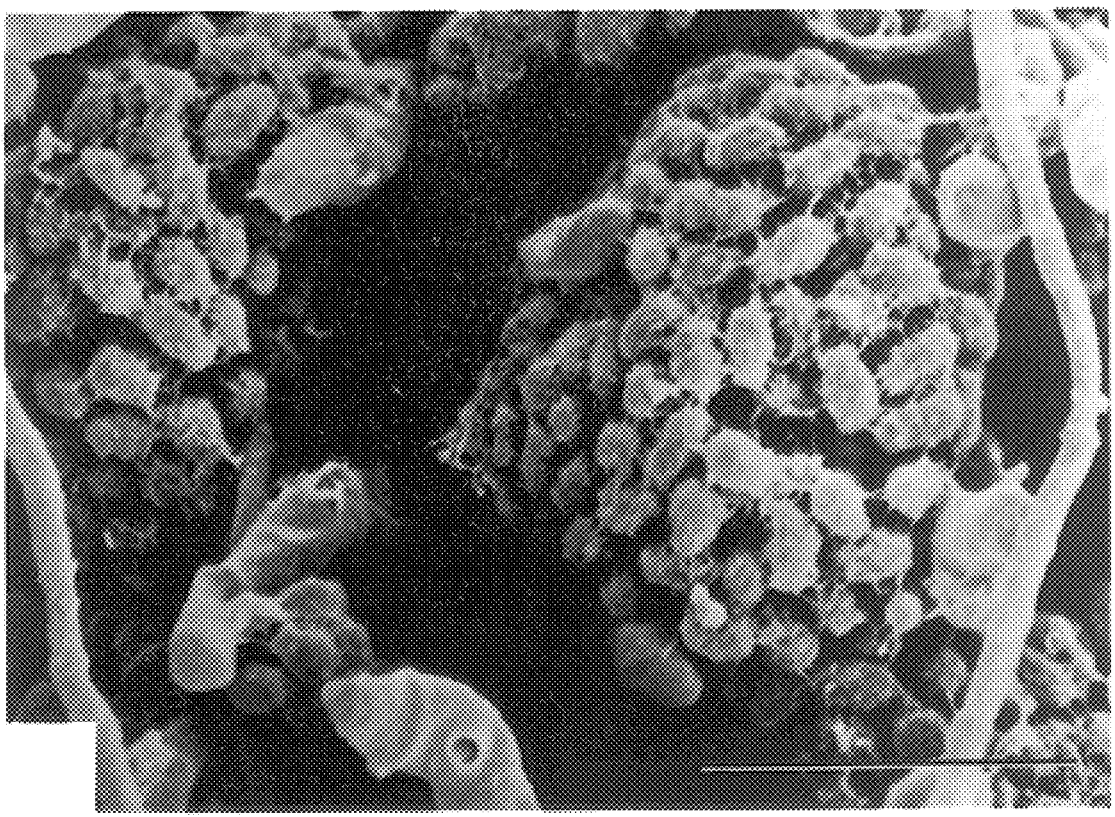
FIG. 6 shows a scanning electron micrograph of single bulbil of *T. andreanae* illustrating the organization of the cells of the bulbil; Bar=10 μm.
Figure 7:
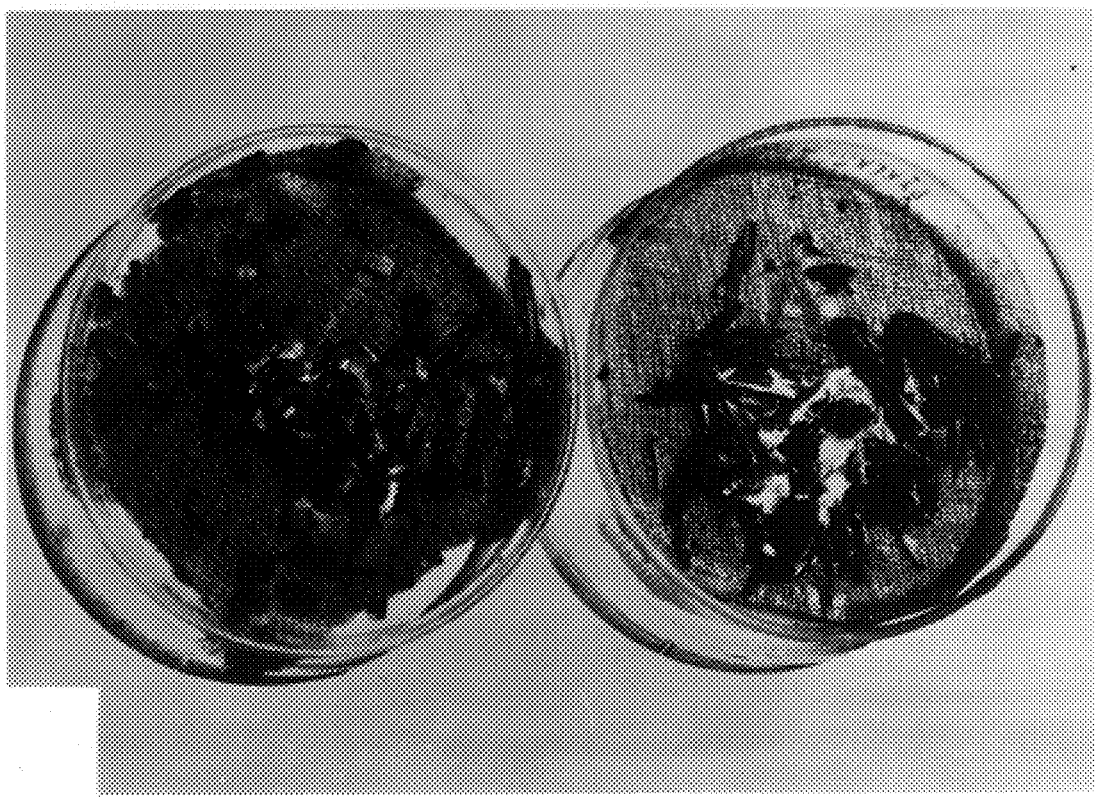
FIG. 7 shows the growth of *T. andreanae* on the inner bark of Pacific yew (left) and growth and bulbil formation on the leaves in small lymph fragments of *T. andreanae* (right).
Figure 9:
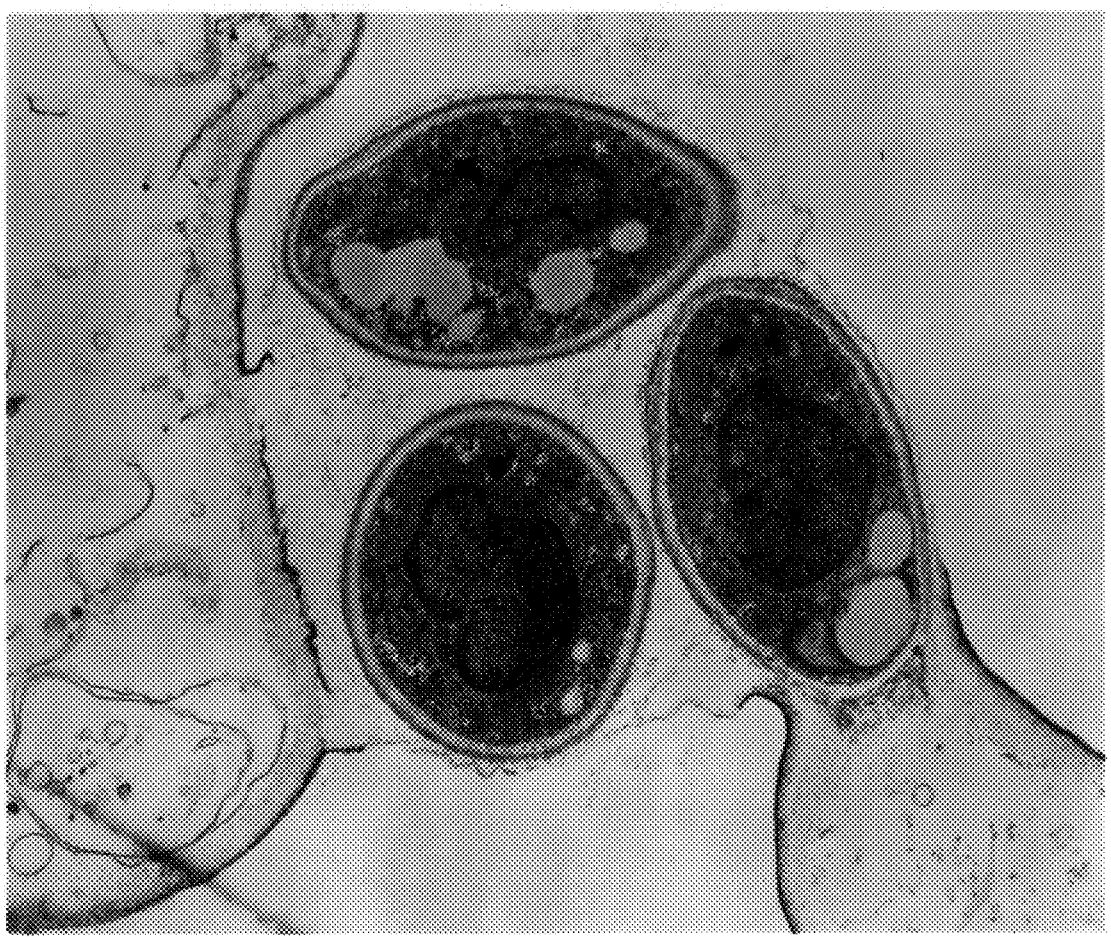
FIG. 9 shows the transmission electron micrograph of *T. andreanae* bulbil cells at a higher magnification. Note that the cell wall has two distinct layers, and a fibrous material between the cells; Bar=1 μm.

The "clumps" of cells in FIGS. 5 and 6 are not located on sterigmata, but seem to arise by a "budding process" (FIG. 6). Number of cells in each clump varies widely (FIGS. 5 and 6). These "clumps" are referred to as bulbils after the broad definition of deBary (Comparative Morphology and Biology of the Fungi, Mycetozoa and Bacteris," English Translation, Clarendon Press, Oxford) , that is, "small pluricellular bodies incapable of germination". In *T. andreanae*, the cells of the bulbils, unlike most bulbilliferous fungi, appear to be loosely packed, but nevertheless connected with fibrous material (FIGS. 6, 9). These clumps of cells might also be considered as conidial masses but since germination has never been observed (in sterile H$_2$O and nutrient broth), the clumps of cells seem to better fit the broad description of a bulbil.

Figure 8:
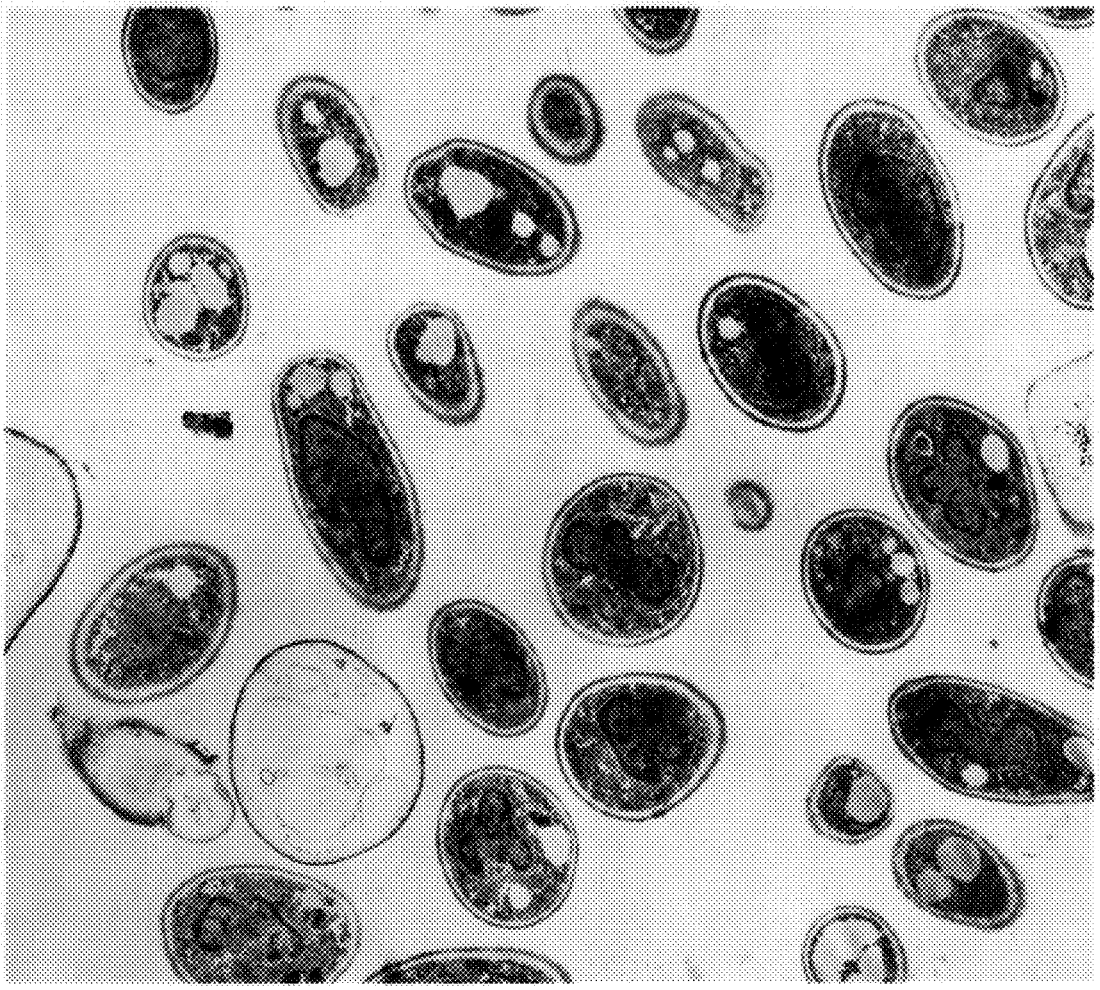
FIG. 8 shows the transmission electron micrograph of bulbil cells of *T. andreanae* illustrating a dense cytoplasm in each cell; Bar=1 μm.

Furthermore, transmission electron microscopic examination of these bulbil cells reveals that they are engorged with cytoplasmic structures including lipid bodies (FIGS. 8, 9). They also possess a bilayered cell wall (FIGS. 8, 9). Nevertheless, these bulbils differ from the bulbils of other standard bulbilliferous fungi by lacking pigmentation, certain sclerotial-like qualities (outer rind-like cells and inner swollen cells) and in the manner of their formation.

EXAMPLE 4

A pure culture species was obtained which was named *Taxomyces andreanae* S2. The fungus species was isolated from the upper limbs of a shrub-like Pacific yew tree growing as undercover in a mature undisturbed cedar forest in Flathead County, Montana as described in Example 1, above. Small limbs (0.5–1.0 centimeter) were surface treated with 70 percent ethanol. The outer bark was peeled back and pieces of the white inner barks (phloem/cambium) were aseptically removed and placed on H$_2$O agar. Hyphal tips of fungi growing from the pieces of the plant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco, e.g., potato dextrose broth agar, nutrient agar, oatmeal agar, cornmeal agar, lima bean agar, water agar, and malt agar.

The fungal culture of *Taxomyces andreanae* S2, was tested and found to produce taxanes by the procedures described above.

EXAMPLE 5

A pure culture species was obtained which was named *Taxomyces andreanae* S3. The fungus species was isolated from the upper limbs of a shrub-like Pacific yew tree growing as undercover in a mature undisturbed cedar forest in Flathead County, Montana as described in Example 1, above. Small limbs (0.5–1.0 centimeter) were surface treated with 70 percent ethanol. The outer bark was peeled back and pieces of the white inner barks (phloem/cambium) were aseptically removed and placed on H$_2$O agar. Hyphal tips of fungi growing from the pieces of the plant were placed on mycological agar and fungal growth was enhanced.

The growth pattern of the fungus was studied on other additional plant species. Leaf, stem, and bark samples of various plant species growing near the tree from which this fungus was obtained were collected near the Hungry Horse dam site on the Flathead National Forest. Small pieces (0.5–2 cm) of leaves, stems and barks of these species were placed over four layers of cheesecloth, thoroughly dampened, and autoclaved. Agar blocks (1.0×1.0 cm) supporting fungal growth were then placed on the sterilized plant material and fungal growth was observed and measured after one week. The growth of the fungus was measured daily after placement of 0.5×0.5 cm agar blocks on standard freshly prepared agar media plates (Difco), e.g., potato dextrose broth agar, nutrient agar, oatmeal agar, cornmeal agar, lima bean agar, water agar, and malt agar.

The fungal culture of *Taxomyces andreanae* S3, was tested and found to produce taxanes by the procedures described above.

EXAMPLE 6
Cultural Characterization of *Taxomyces andreanae* S1

When an agar plug of inoculum of *Taxomyces andreanae* S1 was placed in the center of most freshly prepared agar plates enriched with various nutrients it grew so rapidly that it reached the edge of the plate in 3 days (cornmeal agar, lima bean agar, nutrient agar, malt agar, oatmeal agar). Bulbils did not form on any of these media up to 6 days after inoculation. However bulbils were noticed on the inoculum piece on the cornmeal agar after 6 days.

Some bulbils were noticed at the edge of the malt agar plate 7 days after inoculation. Numerous fluffy aerial mycelia were especially observed on malt agar and after 6–7 days the mycelium on the malt agar developed a deep reddish-brown coloration and a thick mycelial mat.

When the *Taxomyces andreanae* S1 fungus was placed on the autoclaved leaves, fragments of small limbs and bark taken from various tree species located in the geographical area of *Taxus brevifolia*, the best mycelial growth and bulbil formation occurred on Pacific yew (Table 1, FIG. 4), followed by River birch (*Betula nigra*) (Table 1). In contrast, there was no growth on, or bulbil formation on *Larix occidentalis*, or *Tsuga heterophylla*, (Table 1). Other species differentially support weak fungal growth and light bulbil formation, e.g., *Pinus monticola, Picea engelmanni* (Table 1) These observations suggest the likelihood that some host preference of *Taxomyces andreanae* S1 exists in nature and that it would be unlikely to be found in and on many species other than Taxus or Betula.

This organism appears to be a saprophyte or endophyte with the latter preferred since it was found in association with living tissue. There is no evident gross pathology of the host tree. Furthermore, attempts to use agar blocks infested with *T. andreanae* placed under the bark of yew also failed to cause any disease manifestation.

Also, the thicker hyphae ca. 3.75 µm in dia, typically extended the mycelial mat from one object (leaf or limb fragment or agar block) to another. These might be considered "exploratory hyphae". Careful study of the cultural, mycelial and bulbil characteristics in comparison to other bulbilliferous fungi nicely demonstrated the uniqueness of *Taxomyces andreanae*.

EXAMPLE 7

A fungal microbe designated as BAC-2BD-1 was isolated from the inner bark of a yew tree and grown on M-1-D medium for three weeks. Obtained were dense woolly cream colored mycelium with an irregular spreading pattern, there were no obvious fruiting. The fungal biotype was endophytic.

The cultured fungi were ground and extracted with CH$_2$Cl$_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angstroms) and sprayed with 1% vanillin in sulfuric acid. A spot with the same $R_f$ and color reaction (blue fading to brown) identical to taxol appeared.

EXAMPLE 8

A fungi microbe designated as H21 NA was isolated from the needles of a yew tree and grown on M-1-D medium for three weeks. Obtained were fine, translucent, taupe-colored mycelium with an irregular spreading pattern, fruiting structures being present as small brown-rounded bodies. The fungal biotype was parasitic.

The cultured fungi were ground and extracted with CH$_2$Cl$_2$/MeOH 10:1. The lipophilic residue was then chromatographed on 0.25 mm silica gel plates (Merck) The chromatography was conducted with chloroform/acetonitrile 7:3 v/v and chloroform/methanol 7:1 v/v. The resulting plates were examined under UV (254 angstroms) and sprayed with 1% vanillin in sulfuric acid. A spot with the same $R_f$ and color reaction (blue fading to brown) identical to taxol appeared.

EXAMPLE 9

A fungal microbe designated as H15 NB was isolated from needles of a yew tree showing spots on the needles. This microbe was grown on M-1-D medium for three weeks. Obtained were cream colored fine mycelium, there were no obvious fruiting structures and the culture was felt-like in texture. The fungal biotype was endophytic or parasitic.

The fungi were ground and extracted with CH$_2$Cl$_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v.

The resulting plates were examined under UV (254 angstroms) and sprayed with 1% vanillin in sulfuric acid. A spot with the same $R_f$ and color reaction (blue fading to brown) identical to taxol appeared.

EXAMPLE 10

A fungal microbe designated as 1ND was isolated from the needles of a yew tree, grown on M-1-D medium for three weeks. Obtained were green mycelium spores identical to cladosporium sp. The fungal biotype was endophytic.

The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v.

The resulting plates were examined under UV (254 angstroms) and sprayed with 1% vanillin in sulfuric acid. A spot with the same $R_f$ and color reaction (blue fading to brown) identical to taxol appeared.

EXAMPLE 11

A fungal microbe designated as BAC-1NA-1 was isolated from the needles of a yew tree showing spots on the needles and grown on M-1-D medium for three weeks. Obtained were velvet-like areas on the older mycelial growth and there was no obvious fruiting. The fungi were ground and extracted with $CH_2Cl_2$/MeOH 10:1. The lipophilic residue was then chromatographed on 0.25 mm silica gel plates (Merck). The chromatography was conducted with chloroform/acetonitrile 7:3 v/v and chloroform/methanol 7:1 v/v. The resulting plates were examined under UV (254 angstroms) and sprayed with 1% vanillin in sulfuric acid. A spot with the same $R_f$ and color reaction (blue fading to brown) identical to taxol appeared.

The data set forth in Tables 7–9 indicate additional fungi obtained by the method according to the present invention. The fungi described by these data are capable of producing taxol or related taxanes.

Evidence that the fungi obtained by the method of the present invention produce taxol includes thin layer chromatographic (TLC) comparisons of the organic extracts of these fungi against standard taxol in two solvent systems, as well as specific monoclonal antibody analysis of these extracts.

Of the fungal extracts listed below, extracts 4-73-1, 2, 3, 8, 10, 11, and 12 contained metabolites that behaved in an identical fashion as authentic (yew) taxol when examined by thin layer chromatography (TLC) on silica gel using the following solvent systems: 95-5 ethyl acetate-isopropanol, and 7-3 chloroformacetonitrile. The organic extracts of 4-73-4, 5, 6, 7, and 9 had compounds that exhibited behavior similar to that of taxol.

The differences in TLC behavior obtained above are also reflected in monoclonal antibody testing which confirm that the fungal strains produce taxol or related taxanes. Hawaii Biotechnology Group, Inc. performed monoclonal antibody testing using Competitive Inhibition Enzyme Immunoassay (CIEIA) with monoclonal antibodies which they developed. The monoclonal antibody used to detect taxol had the designation MAB-36C and the monoclonal antibody used for detection of taxane, in general, had the designation MAB-8A10. Thus, two tests were performed which involved an antibody specific to taxol, and an antibody that reacts with generic taxanes.

The data presented in Tables 7–9 sets forth the actual value of taxol and taxanes detected in a given sample by CIEIA (detected) and the value extrapolated per liter of culture volume. The data listed for the 4-73 series in Table 7 indicates taxol producing fungal strains. The values listed under "TOTAL WT." in Table 8 are the same values listed as "Detected" in Table 7.

Also included are the taxol/taxane titers measured for the organic extract of *Taxomyces andreanae* (TA) (4-58) which was analyzed concurrently. These values are lower than usual, and probably reflect the poor growth of this particular batch of the fungus.

All of the data are from fungi grown in media containing bacto-soytone (10 g/L), glucose (30 g/L), sucrose (20 g/L), sodium benzoate (30 mg/L), and sodium acetate (1 g/L). When these fungi were grown in this same media to which 2% yew needle broth was added, the taxol/taxane titers were significantly higher.

The values in Tables 7–9, however, are from extracts which were not adulterated with yew in any way. The production of taxol/taxanes suggested by these data reflects the independent biosynthetic capabilities of these fungi obtained by the method according to the present invention.

TABLE 7

| | | TAXOL | | TAXANE | |
|---|---|---|---|---|---|
| CODE | FUNGUS | Detected (µg/sample) | Extra-polated (µg/L) | Detected (µg/sample) | Extra-polated (µg/L) |
| 4-73-1 | CC45BD | 0.0031 | 0.0183 | 0.4112 | 2.4306 |
| 4-73-2 | CC50NA1 | 0.0031 | 0.0274 | 0.2099 | 1.8597 |
| 4-73-3 | CC50NA2 | 0.0029 | 0.0246 | 0.0099 | 0.0840 |
| 4-73-4 | CC52NC | ND | ND | 0.0069 | 0.0410 |
| 4-73-5 | CC53NA | ND | ND | 0.0016 | 0.0350 |
| 4-73-6 | CC53NA1 | ND | ND | 0.0038 | 0.0274 |
| 4-73-7 | CC53NA2 | ND | ND | 0.0021 | 0.0144 |
| 4-73-8 | CC53NC | 0.0046 | 0.0254 | 0.0184 | 0.1016 |
| 4-73-9 | CC54BA | ND | ND | 0.0043 | 0.0306 |
| 4-73-10 | CC54BE | 0.0032 | 0.0411 | 0.0074 | 0.0950 |
| 4-73-11 | CC57BC2 | 0.0064 | 0.1862 | 0.0078 | 0.2268 |
| 4-73-12 | CC64BB | 0.0035 | 0.0532 | 0.0087 | 0.1352 |
| 4-58 | TA | 0.0080 | 0.0147 | 0.0593 | 0.1093 |

Key:
ND = not detected
TA = *Taxomyces Andreanae*

TABLE 8

TAXOL SPECIFIC CIEIA

| SAMPLE | | WT. (mg) | ASSAYED TAXOL (ug/ml) | N | TOTAL WT. (ug) | (WT/WT) % |
|---|---|---|---|---|---|---|
| 4-62 | A | 6.8 | not detected | | | |
| | B | 8.0 | 0.0093 | 1 | 0.0019 | 0.00002 |
| | C | 7.9 | 0.0440 | 2 | 0.0088 | 0.00011 |
| | D | 7.8 | 0.0314 | 1 | 0.0063 | 0.00008 |
| | E | 7.0 | 0.360 | 1 | 0.0072 | 0.00010 |
| | F | 1.0 | not detected | | | |
| | G | 0.6 | not detected | | | |
| | H | 0.1 | not detected | | | |
| 4-61 | A | 0.8 | not detected | | | |
| | B | 7.0 | 0.213 | 2 | 0.0043 | 0.00006 |
| | C | 7.1 | not detected | | | |
| | D | 7.6 | not detected | | | |
| | E | 7.7 | not detected | | | |
| | F | 8.8 | not detected | | | |
| | G | 7.7 | not detected | | | |
| | H | 8.6 | not detected | | | |
| 4-58 | A | 21.0 | 0.0400 | 2 | 0.0080 | 0.00004 |
| 4-73 | 1 | 4.5 | 0.0155 | 1 | 0.0031 | 0.00007 |
| | 2 | 5.0 | 0.0155 | 1 | 0.0031 | 0.00006 |
| | 3 | 4.7 | 0.0147 | 1 | 0.0029 | 0.00006 |
| | 4 | 5.1 | not detected | | | |
| | 5 | 5.0 | not detected | | | |
| | 6 | 5.3 | not detected | | | |
| | 7 | 4.8 | not detected | | | |
| | 8 | 4.6 | 0.0231 | 1 | 0.0046 | 0.00010 |
| | 9 | 4.2 | not detected | | | |
| | 10 | 5.1 | 0.0158 | 1 | 0.0032 | 0.00008 |

TABLE 8-continued

TAXOL SPECIFIC CIEIA

| SAMPLE | WT. (mg) | ASSAYED TAXOL (ug/ml) | N | TOTAL WT. (ug) | (WT/WT) % |
|---|---|---|---|---|---|
| 11A | 5.7 | 0.0320 | 1 | 0.0064 | 0.00011 |
| 11B | 4.8 | not detected | | | |
| 12 | 4.5 | 0.0173 | | | |

TABLE 9

TAXANE ("generic") CIEIA

| SAMPLE | | WT. (mg) | ASSAYED TAXANE (ug/ml) | N | TOTAL WT. (ug) | (WT/WT) % |
|---|---|---|---|---|---|---|
| 4-62 | A | 6.8 | not detected | | | |
| | B | 8.0 | 0.0383 | 1 | 0.0077 | 0.00010 |
| | C | 7.9 | 0.3595 | 2 | 0.0719 | 0.00091 |
| | D | 7.8 | 0.2314 | 2 | 0.0463 | 0.00059 |
| | E | 7.0 | 0.0569 | 2 | 0.0114 | 0.00016 |
| | F | 1.0 | not detected | | | |
| | G | 0.6 | not detected | | | |
| | H | 0.1 | nat detected | | | |
| 4-61 | A | 0.8 | not detected | | | |
| | B | 7.0 | 0.2618 | 2 | 0.0564 | 0.00081 |
| | C | 7.1 | 0.0140 | 1 | 0.0028 | 0.00004 |
| | D | 7.6 | not detected | | | |
| | E | 7.7 | not detected | | | |
| | F | 8.8 | not detected | | | |
| | G | 7.7 | not detected | | | |
| | H | 8.6 | not detected | | | |
| 4-58 | A | 21.0 | 0.2965 + 0.075 | 4 | 0.0593 | 0.00028 |
| 4-73 | 1 | 4.5 | 2.0560 + 0.18 | 3 | 0.4112 | 0.00914 |
| | 2 | 5.0 | 1.0496 | 2 | 0.2099 | 0.00420 |
| | 3 | 4.7 | 0.0497 | 2 | 0.0099 | 0.00021 |
| | 4 | 5.1 | 0.0343 + 0.006 | 3 | 0.0069 | 0.00013 |
| | 5 | 5.0 | 0.0081 | 1 | 0.0016 | 0.00003 |
| | 6 | 5.3 | 0.0191 | 2 | 0.0038 | 0.00007 |
| | 7 | 4.8 | 0.0105 | 2 | 0.0021 | 0.00004 |
| | 8 | 4.6 | 0.0920 + 0.016 | 3 | 0.0184 | 0.00040 |
| | 9 | 4.2 | 0.0215 | 1 | 0.0043 | 0.00010 |
| | 10 | 5.1 | 0.0372 | 2 | 0.0074 | 0.00015 |
| | 11A | 5.7 | 0.0392 | 2 | 0.0076 | 0.00014 |
| | 11B | 4.8 | 0.0205 | 1 | 0.0041 | 0.00009 |
| | 12 | 4.6 | 0.0446 | 2 | 0.0089 | 0.00019 |

A selected collection of taxol producing microorganisms tested above and further defined below, including 13 fungi and 1 bacterium were deposited with the Agricultural Research Service Culture Collection (NRRL), 1815 North University Street, Peoria, Ill., 61604, U.S.A. under the terms of the Budapest Treaty.

All of the microbes described in this application have been isolated from the bark or needles of the northwest Pacific yew tree, *Taxus brevifolia*. Ten of these microbes have been submitted for deposit at the Northern Regional Research Center (NRRL) in Peoria, Ill. The microbes submitted represented distinct morphotypes, i.e., only one representative of the Genus Penicillium was submitted for deposit, although others have been detected. These are only examples of microbes which produce taxol, others have been obtained by the same method described herein. The deposited cell lines have also been tested using CIEIA immunoassay.

All of these microbes have consistently shown evidence of taxol and/or taxane production based on thin layer chromatography data and repeated immunoassay data obtained at both Hawaii Biotechnology Group, Inc. in Aieia, Hi., and in an in-house assay at Montana State University.

All of the data accrued has been obtained either from microorganisms grown in defined synthetic media, containing no yew broth, or in media to which yew broth has been added. In each data set reported below, media is clearly indicated.

De novo biosynthesis of taxane or taxol by microorganisms 1–14 is shown below. The following descriptions include gross morphology, tissue type, biological activity of organic extract of liquid culture of a particular microbe grown in mycological broth, and compounds which we have isolated and identified from these extracts.

Biological activity is determined by the concentration disk method: each microbe is tested against 2 gram(+) and 3 gram(−) bacteria, and 2 fungi. Zones of inhibition listed are indications of activity. Brine shrimp cytotoxicity is ascertained by $LD_{50}$ of extract towards brine shrimp. "No activity" simply indicates that no activity was observed in these tests in the laboratory, not the absolute absence of biological activity.

Figure 10:
FIG. 10 shows strain 1ND 1000× magnified by electron microscope.

FUNGI: MOLD TYPE 1. 1ND—On M1D (see Table 1) agar: Very fine, highly branched mycelia with tendency to grow into media. Deep bottle-green, velvety appearance to both conidia and conidiophore. Conidia are ellipsoid, two-celled and catenulate, and form in unbranched chains, length≈11 μm, with≈6 μm. Does not germinate at 37° C. "Illustrated Genera of Imperfect Fungi" Eds. H. L. Barnett and Barry B. Hunter used to key fungus to Order Moniliales, Genus Bispora. isolated from the needles of a shrubby yew tree on Sep. 7, 1991. Deposited NRRL Mar. 3, 1994, Accession No. NRRL 21210. Bioactivity: brine shrimp cytotoxic. See FIG. 10.

2. H1RE—On M1D agar: Very fine, highly divided, off-white mycelia growing into the medium. Dense, thick pale grey conidiophores cover plate within 7 days. Tentatively identified as Genus Penicillium. Isolated from the roots of a healthy shrubby yew tree. Bioactivity: antibacterial, antifungal, brine shrimp cytotoxic. Compounds isolated to date: phomopsolides. Deposited NRRL Mar. 3, 1994, Accession No. NRRL 21208.

Figure 11:
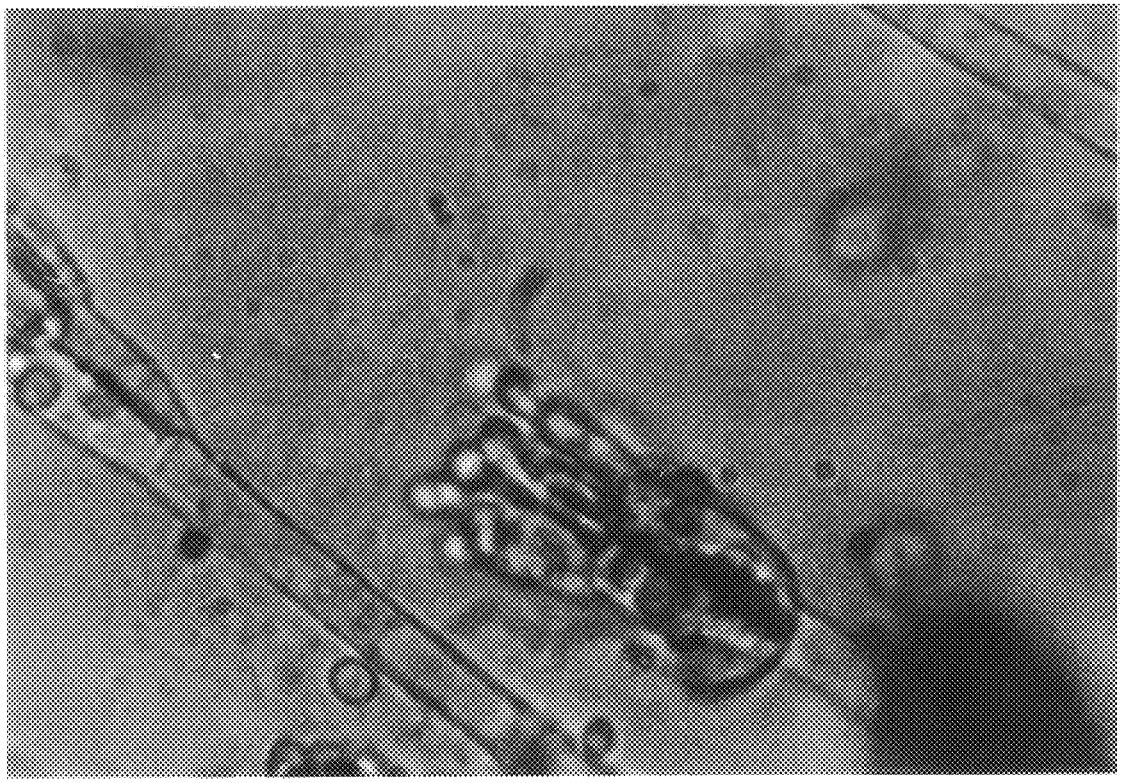
FIG. 11 shows strain H10BA2 1000× magnified by electron microscope.
Figure 12:
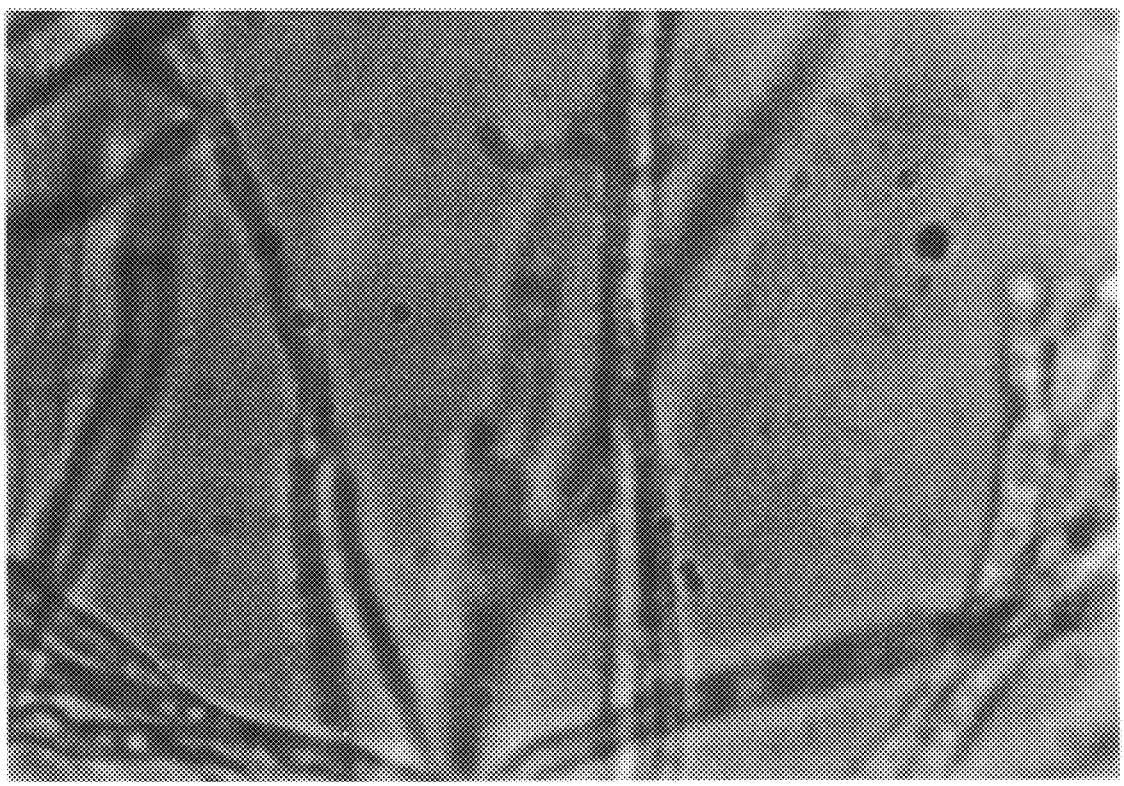
FIG. 12 shows strain WIC65NC 1000× magnified by electron microscope.

3. H10BA2—On M1D agar: Very fine, highly branched off-white mycelia growing down into the medium. Velvety pale green conidiophore with smooth conidia, 2.4×2.4 μm. Fungus keyed to Genus Penicillium by Dr. Rajinder Siddhu. Isolated from bark of shrubby yew tree. Deposited NRRL Mar. 3, 1994, Accession No. NRRL 21209. Bioactivity: antibacterial, antifungal, brine shrimp cytotoxicity. Compounds isolated to date: penitrem A & B. See FIG. 11.

Figure 13:
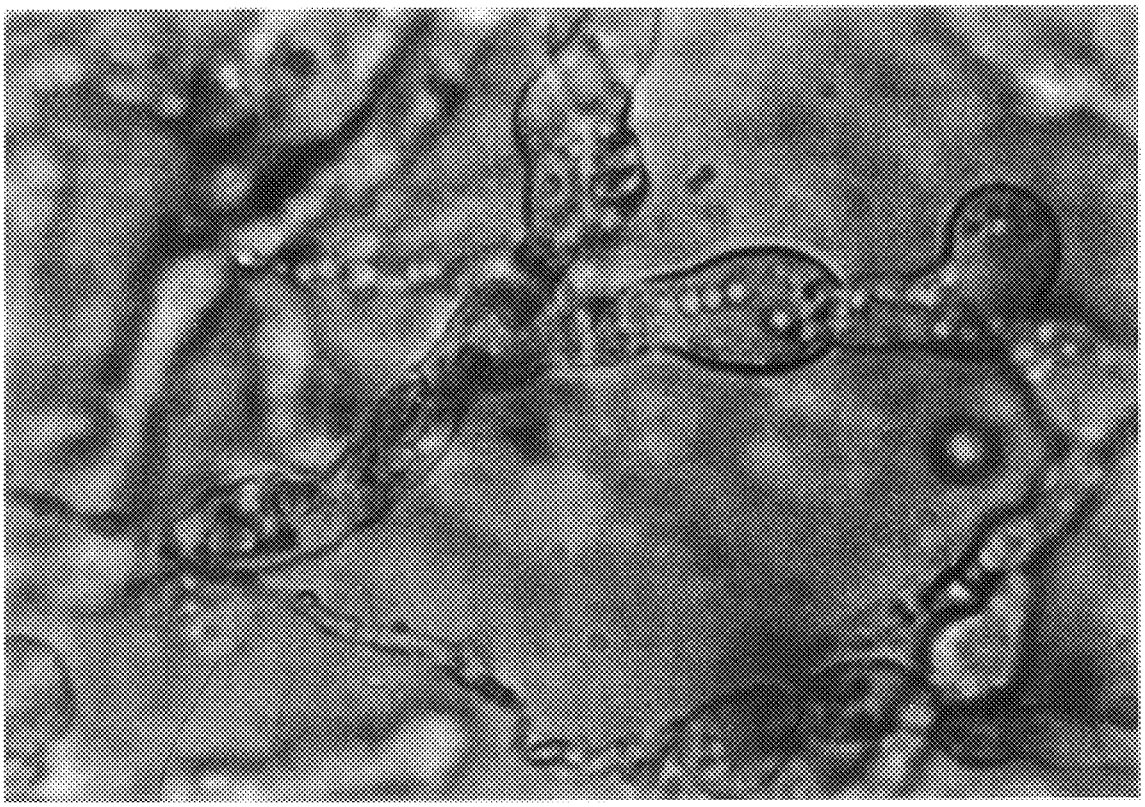
FIG. 13 shows strain CC45BD 1000× magnified by electron microscope.

4. CC45BD—On M1D agar: fine, white, branched, septate mycelia, with dark green spores forming after 96 hours. Little or no aerial growth. On mycological agar: mycelia is denser and tends to aerial growth; green spores not formed. Isolated from the inner bark of a 26" yew tree. Deposited NRRL Mar. 3, 1994, Accession No. NRRL 21207. Biological activity: antibacterial. See FIG. 13.

Figure 14:
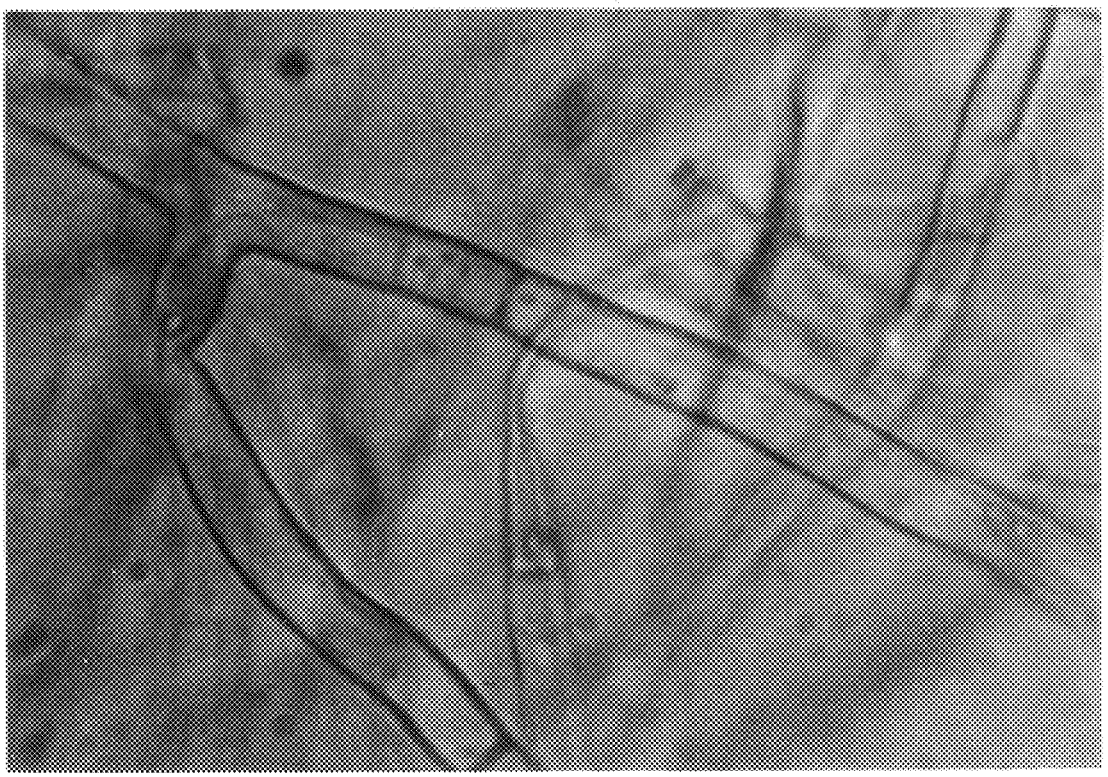
FIG. 14 shows strain CC50NA1 1000× magnified by electron microscope.

5. CC50NA1—On M1D agar: Off-white mycelia with long, intertwining, branched, septate, filamentous hyphae, and irregular edge. Like *Taxomyces andreanae*, hyphae appear to be of two different sizes. Consistent aerial growth throughout plate gives a "fuzzy" appearance. White bulbils are formed along the length of the hyphae. Isolated from healthy needles of a yew tree. Deposited NRRL Mar. 3, 1994, Accession No. NRRL 21204. Biological activity: antibacterial. See FIG. 14.

6. CC50NA2—similar to CC50NA1, but thicker, fuzzier mycelia.

7. CC50NB—On M1D agar: Fine, off-white, highly divided mycelia growing into the medium. Deep green velvety conidiophore form after 2 days. Smooth conidia: 4.8×4.8 µm; smooth stipe: 24×4.8 µm, with enlarged apice; metula: 9.6–12.0 m; phialide: 7.2 µm. Keyed to Genus Penicillium. Isolated from healthy needles of a 24" yew tree. Bioactivity: antibacterial, antifungal, brine shrimp cytotoxic. Compounds isolated to date: gliovictin, compactin, griseofulvin, dechlorogriseofulvin, kojic acid.

Figure 19:
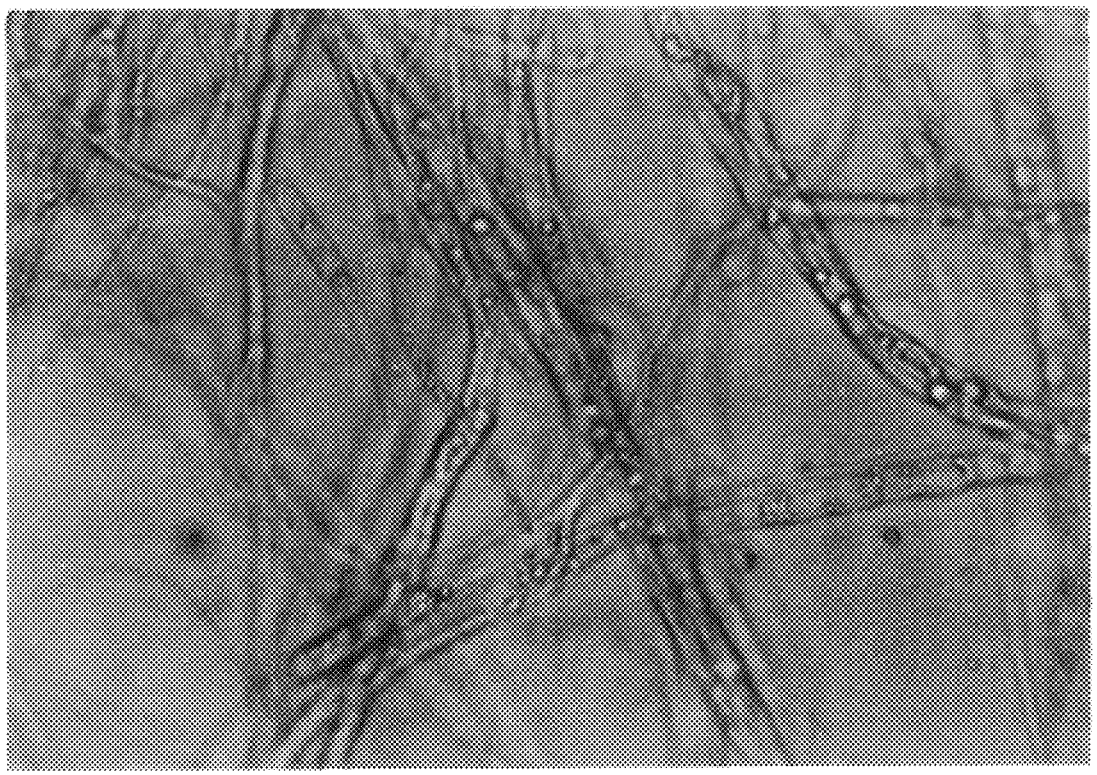
FIG. 19 shows strain CC52NC 1000× magnified by electron microscope.

8. CC52NC—On M1D agar: White, finely divided, highly branched, irregularly edged mycelia with intermittent aerial habit. Aerial hyphae have short "clusters" at regular intervals. Isolated from the healthy needles of a 26" yew tree. Deposited NRRL Mar. 3, 1994, Accession No. NRRL 21212. Biological activity: no activity. See FIG. 19.

Figure 18:
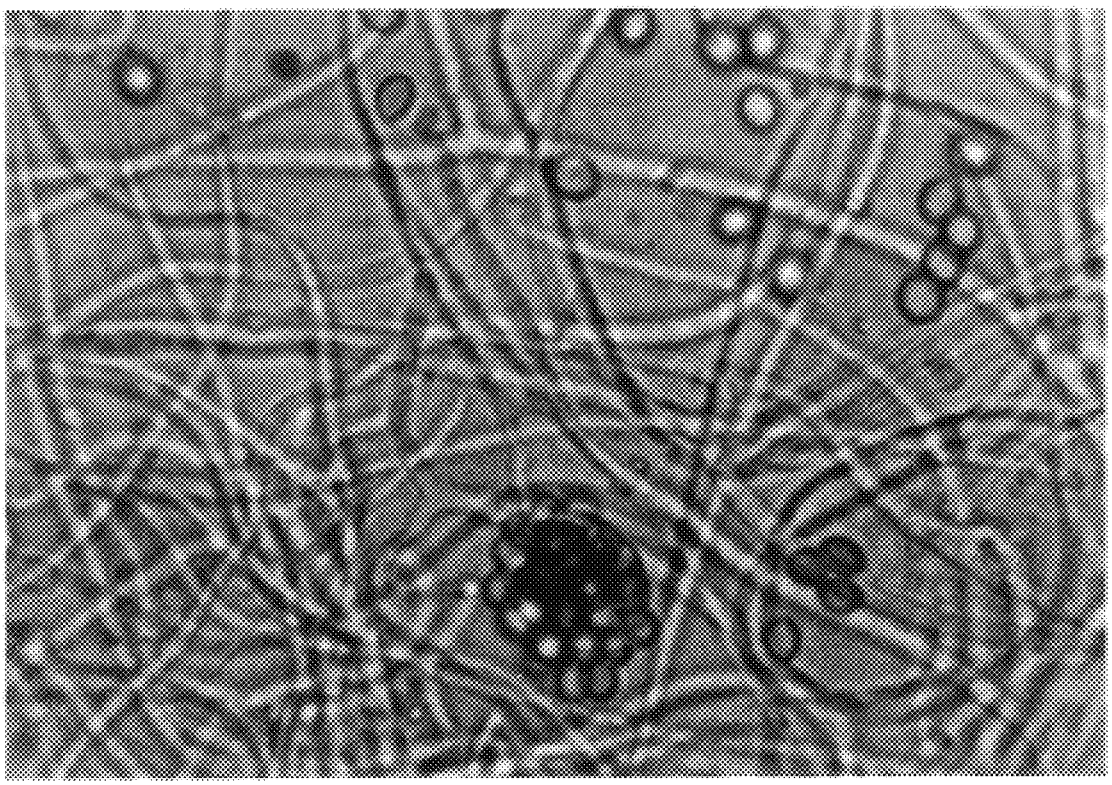
FIG. 18 shows strain CC53NA-2 1000× magnified by electron microscope.

9. CC53NA2-1—On M1D agar: Cream colored mycelia with dense, velvety patches of cream to tan, surrounded by deep green, with dark green spores. Thick aerial pycnidia form in cultures after 2 weeks. These are white with a brown core. Tentatively identified as a Xylaria sp. Liquid cultures grown in M1D broth grow quickly and form a thick, syrupy, pink exudate. Isolated from the needles of a 26" yew tree. Biological activity: no activity. See FIG. 18.

Figure 17:
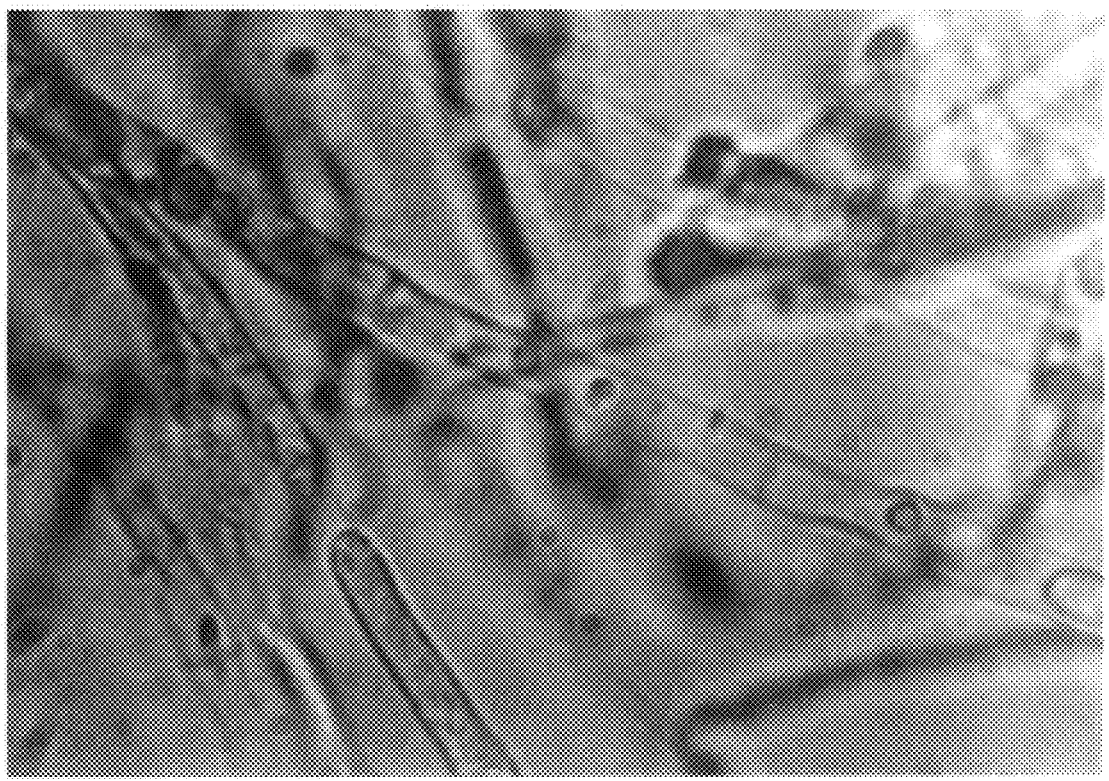
FIG. 17 shows strain CC54BA 1000× magnified by electron microscope.

10. CC54BA—On M1D agar: Dense, fuzzy mycelial mat consisting of fine, long, thin, branched septate hyphae with terminal and mid-strand budding. Turns rich salmon pink after 5 days. Isolated from the inner bark of an 18 inch yew tree. Deposited NRRL Mar. 3, 1994, Accession No. NRRL 21205. Biological activity: slightly antibacterial, brine shrimp cytotoxic. See FIG. 17.

Figure 15:
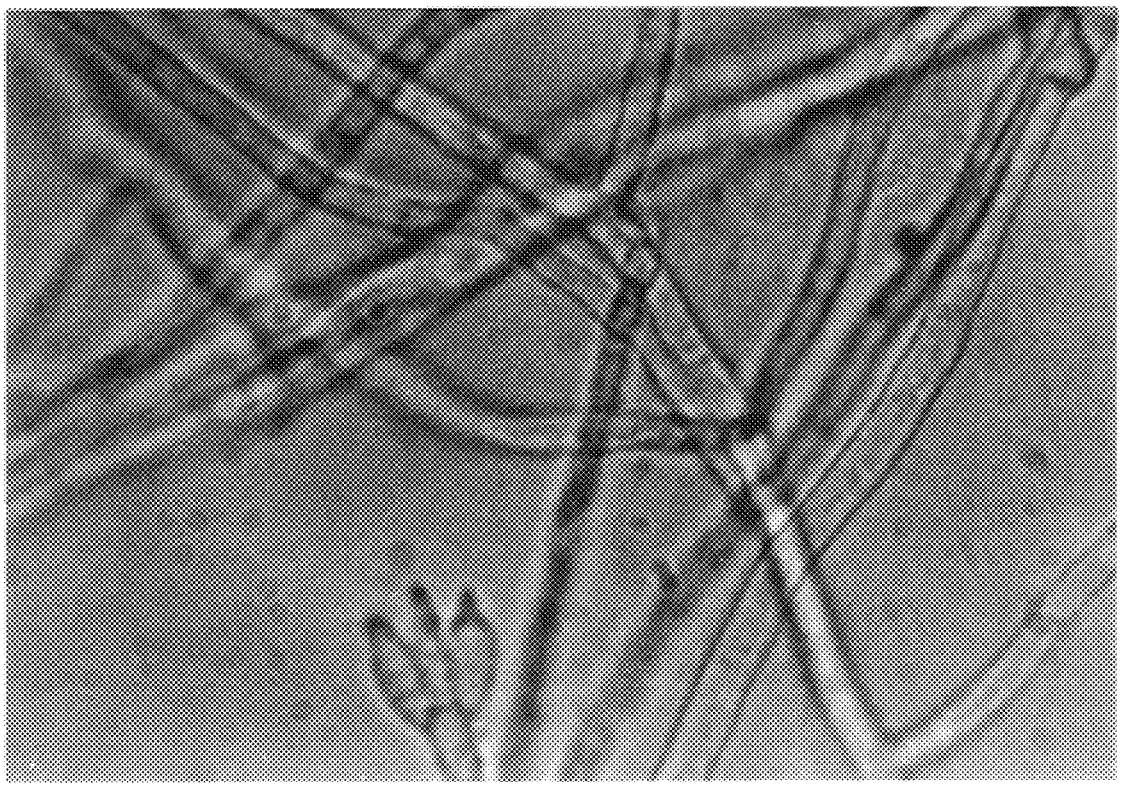
FIG. 15 shows strain CC54BE 1000× magnified by electron microscope.

11. CC54BE—On M1D agar: Dense, fuzzy white mycelial mat with long, thin, sepatate, filamentous hyphae with little branching. Isolated from the bark of an 18" yew tree. Deposited NRRL Mar. 3, 1994, Accession No. NRRL 21211. Biological activity: slightly antibacterial, brine shrimp cytotoxic. See FIG. 15.

12. CC57BC-1—on M1D agar: Velvety green appearance, typical of Penicillium sp. The microorganism was isolated from 28" yew tree bark. Bioactivity: antibacterial, antifungal, brine shrimp cytotoxic. Compounds isolated to date: mycophenolic acid.

Figure 16:
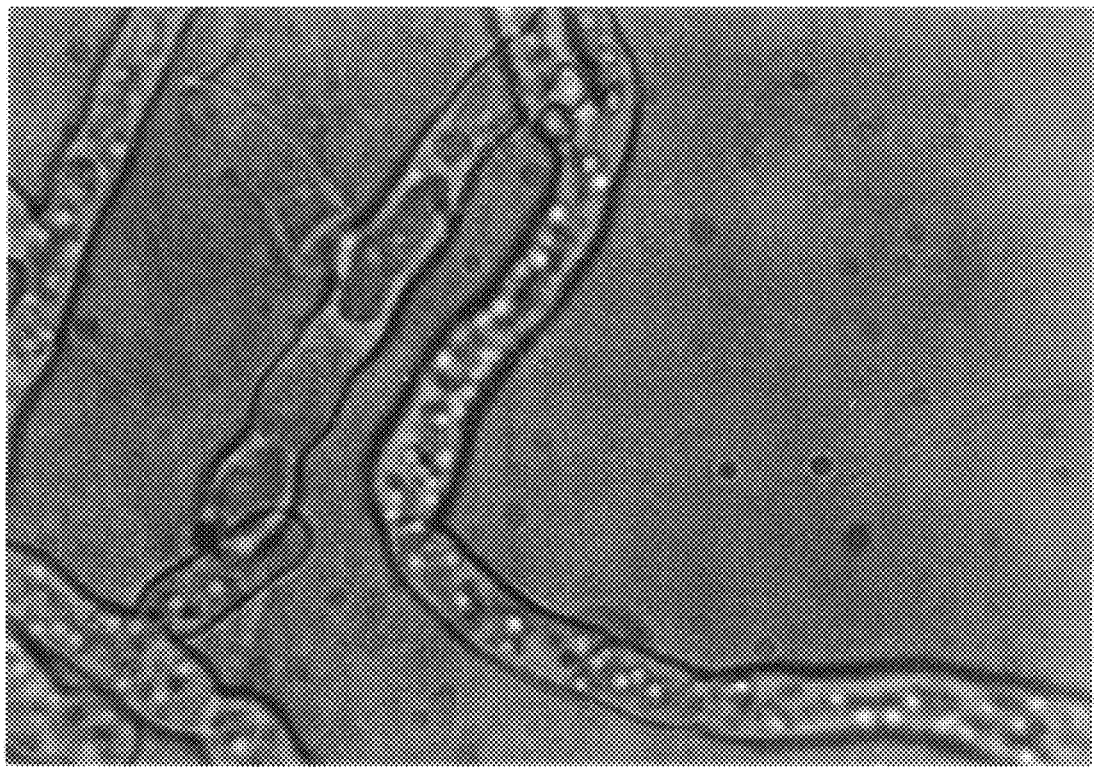
FIG. 16 shows strain CC64BB 1000× magnified by electron microscope.

13. CC64BB—On M1D agar: Fine white mycelial mat consisting of long, thin, branched, septate mycelia. Mycelia develops aerial habit towards edge of late, forming fluffy white mycelial "clusters" after 5 days of growth. Isolated from 28" yew tree bark. Deposited NRRL Mar. 3, 1994, Accession No. NRRL 21206. Biological activity: antibacterial, brine shrimp cytotoxic. See FIG. 16.

BACTERIA

14. CC48BB—On Tryptic soy agar or penassay antibiotic agar: Creamy, regular colonies, gram (+) cocci. Isolated from 18" yew tree bark. Identified by Dr. Eid Megeed as a Micrococcus sp. Biological activity: antibacterial, brine shrimp cytotoxic.

A. Additional CIEIA testing was performed to conform the production of taxol or taxane by the microorganisms. See Table 10.

B. The microbes were grown in yew free media to examine the "uninduced" potential of microbes to make taxol/taxanes. Organisms were grown in mycological broth (soytone and glucose only). The culture volume was 1 Liter, so volume factor was not necessary for estimation of /Liter titers. However, only a portion of extract was used, and this factor was included in the extrapolation to /Liter titers. See Table 11.

CIEIA DATA

For all of the fungi we determined taxol and taxane titers in term of µg/L and µg/g dry mycelia weight. We only determined titers in ug/L for the single bactereum, CC48BB.

A. HAWAII BIOTECHNOLOGY GROUP, INC.

Tested microbes grown in mycological broth+2% yew broth, 100 ml. each. Taxol and Taxane/L are extrapolated by multiplying/fraction values by 10 if entire extract was tested. If only ½ of the extract was tested, then/fraction titer was multiplied by 20 to obtain/l. value. The blank medium, which consisted of 1 l. of uninoculated mycological broth+ 2% yew broth, obviously did not need extrapolation for the/Liter titer.

TABLE 10

| | $CH_2Cl_2$ ext. | taxol/ fraction (ug) | taxol/ liter (ug/L.) | Specific activity taxol/dry wt. mycelia (ug/g) | taxane/ fraction (ug) | taxane/ liter (ug/L.) | Specific activity taxane/dry wt. mycelia (ug/g) |
|---|---|---|---|---|---|---|---|
| CC45BD | 0.0027 | 0.408 ug | 4.08 ug | 20.40 | 1.67 ug | 10.67 ug | 53.35 |
| CC48BB | 0.0045 g | 0.518 | 5.18 | | 5.63 | 56.3 | |
| CC50NA1 | 0.0045 | 0.462 | 4.62 | 0.56 | 5.22 | 52.2 | 6.29 |
| CC50NA2 | 0.0022 | 0.880 | 8.80 | 2.83 | 8.96 | 89.6 | 28.90 |
| CC52NC | 0.0024 | 0.758 | 7.58 | 25.26 | 7.96 | 79.6 | 265.33 |
| CC53NA | 0.0012 | 0.622 | 6.22 | 1.38 | 7.27 | 72.7 | 16.16 |
| CC53NC | 0.0020 | 0.614 | 6.14 | 1.06 | 5.65 | 56.5 | 9.74 |
| CC54BA | 0.0074 (½) | 0.304 | 6.08 | 1.41 | 4.20 | 84.0 | 19.53 |
| CC54BE | 0.0056 (½) | 0.174 | 3.48 | 0.84 | 1.82 | 36.4 | 8.88 |
| CC57BC2 | 0.0065 (½) | 0.192 | 3.84 | 1.16 | 3.59 | 71.8 | 21.75 |
| CC64BB | 0.0060 | 0.264 | 2.64 | 1.39 | 1.87 | 37.4 | 19.68 |
| blank(H.) | 0.0057 | 0.95 | 0.95 | | 6.61 | 6.6 | |

******

TABLE 11

|         | CH$_2$Cl$_2$ sample (g) | total wt (g) | taxol/ sample (ug) | taxol/ Liter (ug/L) | Specific activity taxol/dry wt. mycelia (ug/g) | sample (ug) | taxane/ Liter (ug/L) | Specific activity taxane/dry wt. mycelia (ug/g) |
|---------|---------|---------|---------|---------|---------|---------|---------|---------|
| CC45BD  | 0.0045  | 0.0266  | 0.0031  | 0.018   | 0.020   | 0.4112  | 2.43    | 2.80    |
| CC50NA1 | 0.0050  | 0.0443  | 0.0031  | 0.027   | 0.019   | 0.2099  | 1.86    | 1.30    |
| CC50NA22| 0.0047  | 0.0399  | 0.0029  | 0.025   | 0.266   | 0.0099  | 0.840   | 8.96    |
| CC52NC  | 0.0050  | 0.0303  | nd      |         |         | 0.0069  | 0.042   | 8.571   |
| CC53NA  | 0.0050  | 0.1092  | nd      |         |         | 0.0016  | 0.035   | 0.016   |
| CC53NC  | 0.0046  | 0.0254  | 0.0046  | 0.025   | 0.029   | 0.0184  | 0.102   | 0.120   |
| CC54BA  | 0.0042  | 0.0299  | nd      |         |         | 0.0043  | 0.031   | 0.023   |
| CC54B1  | 0.0051  | 0.0655  | 0.0032  | 0.041   | 0.856   | 0.0074  | 0.095   | 0.081   |
| CC57BC2 | 0.0057  | 0.1658  | 0.0064  | 0.186   | 0.086   | 0.0078  | 0.227   | 0.105   |
| CC64BB  | 0.0046  | 0.0699  | 0.0035  | 0.053   | 0.053   | 0.0089  | 0.135   | 0.135   |

C. H10BA2 grown in 26 L mycological broth without added yew broth. Estimate of 1 L titer includes volume factor. See Table 14.

Thus all of the exemplary taxol or taxane producing microorganisms set forth herein were obtained by the general method of the invention and found to produce taxane or taxol.

Taxol produced by any of the above microorganisms can be used in the treatment of cancers, including, but not limited to lung cancer, ovarian cancer, breast cancer, prostate cancer and melanoma, as well as others. See for example, Holmes et al., "Phase II trial of taxol, an active drug in the treatment of metastatic breast cancer", J. Natl. Cancer Inst., Vol. No. 83, No. 24., Dec. 1991, p. 1797–1805; Rowinsky et al., "Cardiac disturbances during the administration of taxol", J. Clinical Oncol., vol 9, No. 9, Sept. 1991, pp. 1704–1712; Brown et al., "Phase I trial of taxol given by a 6 hour intravenous infusion", J. Clinical. Oncol., Vol 9, No. 7, p. 1261–67; "Ovarian Cancer", Semin. Surg. Oncol, Vol. 6, No. 6, p. 328–38; Thigpen et al., "Chemotherapy in ovarian carcinoma: present role and future prospects, Semin. Oncol., vol 16, (4 Suppl. 6), Aug. 1989, p. 58–65; Roytta et al. "Morphological studies on the effect of taxol on cultured human prostatic cancer cells, Prostate 1987, Vol 11 (1), p. 95–106; McGuire et al., "Taxol: a unique antineoplastic agent with significant activity in advanced ovarian epitelial neoplasms" Ann Inter. Med. vol 111 (4), Aug. 1989, p. 273–279. and Wiernik et al., "Phase I clinical and pharmacokinetic study of taxol", Cancer Res., Vol. 47, No. 9, (May 1, 1987) p. 2486–93.

B. MONTANA STATE UNIVERSITY

These results were obtained

Fungi were grown in mycological broth without any yew added. IND was 2 l., H10BA2 was 10l., CC50NA1 and CC50NA22 were 1 l.. Appropriate factoras are used to extrapolate to/Liter titers.

TABLE 12

|         | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---------|---------|---------|---------|---------|---------|---------|---------|---------|
| IND     | 0.016 g | 0.0403  | 0.0029  | 0.0042  | 0.001   | 0.0058  | 0.0083  | 0.002   |
| H10BA2  | 0.0085  | 0.9249  | 0.0015  | 0.0163  | 0.002   | 0.0879  | 0.9565  | 0.143   |
| CC50NA1 | 0.0142  | 0.0499  | 0.0025  | 0.0088  | 0.014   | 0.0067  | 0.0234  | 0.036   |
| CC50NA22| 0.0135  | 0.0463  | 0.00298 | 0.0102  | 0.039   | 0.0074  | 0.0254  | 0.102   |

******

These were tested
Fungi were grown in media 1 (soytone, yeast, vitamins) and 2% yew broth in 500 ml. cultures.

TABLE 13

|         | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---------|---------|---------|---------|---------|---------|---------|---------|---------|
| CC50NA22| 0.0046 g| 0.0146 g| 0.0592 ug| 0.376 ug| 0.313  | 0.282 ug| 1.790 ug| 1.49   |
| CC53NA1 | 0.0093  | 0.0193  | 0.0327  | 0.135   | 0.259   | 0.241   | 1.003   | 1.93    |
| 4BA     | 0.0083  | 0.0198  | 0.0576  | 0.274   | 1.827   | 0.377   | 1.798   | 11.99   |
| H10BA2  | 0.0171  | 0.0366  | 0.0135  | 0.058   | 0.009   | 0.276   | 1.189   | 0.175   |
| CC50NA1 | 0.0071  | 0.0137  | 0.173   | 0.669   | 0.372   | 0.279   | 1.077   | 0.598   |
| Blank   | 0.0045  | 0.0045  | 0.149   | 0.149   |         | 0.307   | 0.307   |         |

*****

Tested
H10BA2 grown in 26 l. mycological broth without added yew broth. Estimate of 1 l. titer includes volume factor. Second sample, H10BA2 grown in 1 l. broth, also without added yew broth.

TABLE 14

| | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| H10BA2 | 0.0114 | 1.3142 | 0.1389 | 0.600 | 0.16 | 0.107 | 0.316 | 1.4010.244 |
| H. | 0.0103 | 0.0442 | 0.1284 | 0.549 | 0.190 | | | |

\*\*\*\*\*\*

These samples were
Fungi were grown in 4×100 mL. media 1 and 1% yew broth.

TABLE 15

| | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC52NC | 0.0064 | 0.0530 | 0.0923 | 1.910 ug | 2.94 | 0.2648 ug | 5.48 ug | 8.431 |
| CC45BD | 0.0040 | 0.0484 | 0.0236 | 0.714 | 0.193 | 0.1655 | 5.006 | 1.353 |
| Blank | 0.0085 | 0.0090 | 0.243 | 0.257 | | | | |

\*\*\*\*\*\*

These samples were 500 ml., media 1 and 1% yew broth.

TABLE 16

| | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC50NB | 0.0060 | 0.0977 | 0.0063 | 0.206 | 0.089 | 0.0398 | 1.30 | 0.568 |
| CC564BB | 0.0053 | 0.0252 | 0.0243 | 0.31 | 0.481 | 0.0744 | 0.707 | 1.473 |
| IND | 0.0102 | 0.0304 | 0.0175 | 0.103 | 0.057 | 0.0728 | 0.425 | 0.233 |
| 4BA | 0.0125 | 0.0194 | 0.3396 | 1.054 | 7.027 | 1.1420 | 3.544 | 23.63 |

\*\*\*\*\*\*

Cultures were grown in 250 ml. tryptic soy broth with 1% yew needle broth added.

TABLE 17

| | CH$_2$Cl$_2$ sample (g) | total wt (g) | taxol/ sample (ug) | taxol/ Liter (ug/L) | Specific activity taxol/dry wt. mycelia (ug/g) | taxane/ sample (ug) | taxane/ Liter (ug/L) | Specific activity taxanes/dry wt. mycelia (ug/g) |
|---|---|---|---|---|---|---|---|---|
| CC48BB | 0.0112 | 0.0225 | 0.0143 | 0.115 | | 0.266 | 2.138 | |
| | 0.0106 | 0.0220 | 0.0109 | 0.091 | | 0.245 | 2.054 | |
| Blank | 0.0055 | 0.0055 | 0.0139 | 0.074 | | | | |
| | 0.0066 | 0.0454 | 0.0064 | 0.177 | | 0.007 | 0.193 | |
| | 0.0073 | 0.0465 | 0.0038 | 0.098 | | 0.0051 | 0.130 | |
| Blank | 0.0040 | 0.0331 | 0.0025 | 0.024 | | 0.007 | 0.069 | |

All publications cited herein are incorporated by reference herein in their entireties.

Taxol is administered in acceptable formulations as set forth in Remingtons Pharmaceutical Sciences, 18th Ed., incorporated herein by reference. Taxol formulations may comprises from about 0.01 to 99% taxol, and may preferably be in dosages of about 50 mg/m2 to about 300 mg/m2, which is the maximum dose-limiting toxicity for peripheral neuropathy. Dosage times known to those of skill in the art may be used. A 6-hour IV infusion every 21 days is preferred.

Due to the pioneering nature of the present invention, one of skill in the art readily recognizes that the present invention also encompasses a process for isolating a fungus which produces a pharmaceutical product derived from plant material which comprises the steps of:

(a) obtaining tissue fragments from plant material which is the origin of said pharmaceutical product;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said chromatographic solvent to form a solution;

(g) checking the solution for presence of the pharmaceutical of interest, and (h) isolating the fungal cultures which produce the pharmaceutical product.

In addition, the present invention enables a process for obtaining a pharmaceutical product derived from plant material which comprises the steps of:

(a) obtaining tissue fragments from plant material which is the origin of the pharmaceutical product;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said solvent solution; and (g) checking the solution for presence of the pharmaceutical of interest.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. All publications cited herein are incorporated by reference in their entireties. It is to be understood that the phraseology or terminology employed herein is for the purpose of description only and not of limitation.

What is claimed is:

1. A method for isolating a microorganism which produces a taxane, which comprises the steps of:

(a) obtaining tissue fragments from a tree of the Genus Taxus;

(b) placing said tissue fragments on agar medium until fungal growth occurs;

(b) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding an organic solvent to the mixture;

(f) obtaining a chromatograph of said fungal culture in said solvent;

(g) checking the solution for the taxane reaction with vanillin-sulfuric spray, and comparing the chromatograph with one or more taxane standards selected from the group consisting of taxol, baccatin and cephalomannine; and (h) selecting a microorganism which produces the taxane.

2. A method according to claim 1, wherein said tree is a species selected from the group consisting of *Taxus brevifolia, Taxus baccata, Taxus cuspiduta, Taxus canadensis*, and *Taxus floridana*.

3. A method according to claim 1, wherein said tree is a member of the species *Taxus brevifolia*.

4. A process for isolating an endophytic fungus which produces a taxane which comprises the steps of:

(a) obtaining tissue fragments from plant material which is the origin of said taxane;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said chromatographic solvent to form a solution;

(g) checking the solution for presence of taxanes; and (h) selecting and isolating the fungal cultures which produce taxanes.

5. A process for obtaining taxane derived from plant material which comprises the steps of:

(a) obtaining tissue from plant material which is the origin of the taxane;

(b) placing said tissue fragments on agar medium until fungal growth occurs;

(c) placing fungal hyphae from said fungal growth on mycological agar until a culture in pure form is obtained;

(d) transferring said fungal hyphae to a fungal lab growth medium, and growing a fungal culture;

(e) removing at least a portion of the culture media containing the fungal culture, thoroughly grinding the mycelium, and adding a chromatographic solvent to the mixture;

(f) obtaining a chromatograph of said fungal culture in said solvent solution;

(g) checking the solution for presence of taxane; and (h) selecting the fungal cultures which produce taxane.

6. A process according to claim 5 wherein said plant material is obtained from a tree of the Genus Taxus.

* * * * *